(12) United States Patent
Fang et al.

(10) Patent No.: US 11,066,476 B2
(45) Date of Patent: Jul. 20, 2021

(54) ASYMMETRIC BISPECIFIC ANTIBODY

(71) Applicant: SHANGHAI TONGJI HOSPITAL, Shanghai (CN)

(72) Inventors: Jianmin Fang, Shanghai (CN); Bingyu Li, Shanghai (CN)

(73) Assignee: SHANGHAI TONGJI HOSPITAL, Shanghai (CN)

( * ) Notice: Subject to any disclaimer, the term of this patent is extended or adjusted under 35 U.S.C. 154(b) by 197 days.

(21) Appl. No.: 16/131,527

(22) Filed: Sep. 14, 2018

(65) Prior Publication Data

US 2020/0087412 A1    Mar. 19, 2020

(51) Int. Cl.
*C07K 16/30*    (2006.01)
*C07K 16/28*    (2006.01)
*A61P 35/00*    (2006.01)

(52) U.S. Cl.
CPC .............. *C07K 16/30* (2013.01); *A61P 35/00* (2018.01); *C07K 16/2863* (2013.01); *C07K 16/2887* (2013.01); *C07K 16/2896* (2013.01); *C07K 2317/56* (2013.01); *C07K 2317/732* (2013.01)

(58) Field of Classification Search
None
See application file for complete search history.

(56) References Cited

U.S. PATENT DOCUMENTS

| | | |
|---|---|---|
| 7,112,324 B1 | 9/2006 | Dorken et al. |
| 7,575,923 B2 | 8/2009 | Dorken et al. |
| 8,268,314 B2 | 9/2012 | Baehner et al. |
| 8,703,130 B2 | 4/2014 | Baehner et al. |
| 9,708,396 B2 | 7/2017 | Baehner et al. |
| 2006/0193852 A1 | 8/2006 | Dorken et al. |
| 2010/0111967 A1 | 5/2010 | Baehner et al. |
| 2012/0321627 A1 | 12/2012 | Baehner et al. |
| 2015/0004166 A1 | 1/2015 | Baehner et al. |
| 2017/0368169 A1* | 12/2017 | Loew ..................... C07K 16/30 |
| 2017/0369566 A1 | 12/2017 | Baehner et al. |

FOREIGN PATENT DOCUMENTS

| | | | | |
|---|---|---|---|---|
| CN | 1299410 A | | 6/2001 | |
| CN | 103936860 A | | 7/2014 | |
| CN | 104592393 A | | 5/2015 | |
| WO | WO 2016/126950 | * | 8/2016 | ............. C07K 16/30 |
| WO | WO-2016126950 A1 | | 8/2016 | |

OTHER PUBLICATIONS

First Chinese Office Action regarding Application No. 201710204748.7 dated Jun. 3, 2020. English translation provided by Unitalen Attorneys at Law.

Ha, Ji-Hee et al., "Immunoglobulin Fc Heterodimer Platform Technology: From Design to Applications in Therapeutic Antibodies and Proteins," Frontiers in Immunology, Oct. 6, 2016, vol. 7 Article 394, pp. 1-16.

Borrock, M.J. et al., "Chain A, Ig Gamma-1 Chain C Region" www.ncbi.nlm.nih.gov/protein/3S76_A.

Guo, Yajun, "Progress in Monoclonal Antibody-Based Immunotherapy for Cancer Treatment," Chinese Journal of Biotechnology, Jun. 25, 2015, pp. 857-870.

* cited by examiner

*Primary Examiner* — Nelson B Moseley, II
(74) *Attorney, Agent, or Firm* — Harness, Dickey & Pierce, P.L.C.

(57) ABSTRACT

The present invention relates to a novel asymmetric bispecific antibody. The present invention also relates to a method for preparing the asymmetric bispecific antibody and a method of treating a disease using the antibody.

17 Claims, 8 Drawing Sheets
Specification includes a Sequence Listing.

ASYMMETRIC BISPECIFIC ANTIBODY

FIELD

The present invention relates to an asymmetric bispecific antibody.

BACKGROUND

Recently, many types of recombinant antibodies have been developed, for example, tetravalent bispecific antibodies obtained by fusion of, for example, class IgG antibodies and single-chained domains. Some other new types of antibodies have also been developed in which the core structure (IgA, IgD, IgE, IgG or IgM) of the antibodies is no longer retained, for example, some single chain antibodies (scFvs, Bis-scFvs), minibodies, and di-, tri- or tetra-antibodies, which are capable of binding to two or more antigens.

Bispecific antibodies are capable of simultaneously binding to two different targets, and bispecific antibodies specific for certain cellular targets have been described to date.

Tumors are one of the major diseases which currently cause human death. Conventional treatment of a tumor relies on surgery, chemotherapy, and radiation therapy, however, most of the patients have developed drug resistance and relapse after chemotherapy. Surgery combined chemotherapy and radiotherapy can prolong the survival time of patients, but many tumor patients have still eventually died of the onset of tumor metastasis. Monoclonal antibodies have a high drug specificity, small toxic side effects and unique biological effects, and have an increasingly important role in the field of tumor targeted therapy. There have been dozens of therapeutic antibody drugs as approved by FDA, US. Among these drugs, antibody drugs, represented by Rituxan, Avastin, Herceptin, etc., have exhibited good efficacy in the treatment of malignant tumors such as breast cancer and colon cancer.

Currently recognized anti-tumor mechanisms of antibodies include inhibition of key signaling, antibody-dependent cell-mediated cytotoxicity (ADCC), and complement dependent cytotoxity (CDC) and the like. Among them, the antibody-dependent cell-mediated cytotoxicity, namely ADCC, is one of the main mechanisms by which the antibodies kill tumor cells. When an antibody binds to an antigen on the surface of a tumor cell, the Fc moiety of the antibody binds to a Fc receptor on the surface of an immune effector cell, which in turn triggers killing of a target cell by the effector cell (e.g., a NK cell). Many monoclonal antibody drugs exhibit the anti-tumor effects mainly through ADCC.

The ADCC effect of common IgG antibodies is often limited in that the IgG Fc has a limited capability to recruit effector cells, and the presence of inhibitory IgG Fc receptors can attenuates the recruitment of the effector cells. A bispecific antibody (BsAb) is an effective approach to enhance the ADCC and has been studied and applied in tumor immunotherapy. For example, Blinatumomab, as approved by FDA, US, is a monoclonal antibody against CD19 and CD3, of which the structure is characterized in that an anti-CD19 single chain antibody (scFv) is directly linked to an anti-CD3 scFv by a linking sequence to form a so-called BiTE (bispecific T cell engager) technology platform. However, Blinatumomab, or bispecific antibodies prepared by the BiTE technology have a very short half-life in vivo, which affects the drug efficacy.

In order to obtain a bispecific antibody with good pharmacological and pharmacokinetic properties, researchers have designed a variety of different bispecific antibodies, most of which have various defects, mainly manifested by: 1) the difficulty of large-scale production, 2) a too short half-life, 3) bivalent binding to immune effector cells, resulting in mutual killing between the immune effector cells. Therefore, although the bispecific antibody is a hotspot in studies on antibody drugs, there are few types of bispecific antibodies being approved for clinical applications, and thus technological innovations are desired.

SUMMARY

The present inventors have designed an asymmetric bispecific antibody having a completely novel structure, which is capable of exhibiting a better anti-tumor effect and significantly improves the defects of existing bispecific antibodies.

In particular, one object of the present invention is to construct a bispecific antibody capable of monovalently binding to an immune effector cell, wherein the bispecific antibody binds to the surface protein of a tumor cell on the one hand and monovalently binds to an immune effector cell on the other hand, that is, one bispecific antibody molecule only binds to one immune effector cell to thereby avoid mutual killing between the effector cells. At the same time, it must be ensured that such a bispecific antibody has a good half-life in vivo.

T cell immune response is an important part of the human immune system, and thus, construction of antibodies bispecific to T cells and tumor cell surface antigens can activate inactive T cells to kill a targeted tumor, thereby achieving the treatment of the malignant tumor, wherein a T cell surface antigen CD3 can be used as a target. In addition thereto, surface markers of other immune effector cells can also serve as targets for the bispecific antibodies. Studies have shown that an IgA receptor FcαRI (CD89), which is expressed on neutrophils, monocytes, macrophages, eosinophils, and dendritic cells (DCs), mediates various immune effects between IgA and myeloid cells such as neutrophils, mononuclear macrophages. The neutrophils are the most abundant leukocytes, and the number of neutrophils accounts for about 55%~70% of the total number of leukocytes in the adult blood. The neutrophils can more effectively mediate a tumor killing response. Therefore, bispecific antibodies using CD89 cells as effector cells are also of interest.

Tumor surface antigens CD19 and CD20 are both non-glycosylated transmembrane proteins with high conservation. CD19 and CD20 are expressed in most of B lymphocytes, but not expressed in plasma cells, lymphoid stem cells and other tissues. More than 95% of the B cell lymphomas have CD19 and CD20 expressions and have no significant endocytosis and shedding, and these characteristics allow the CD19 and CD20 to be ideal target antigens for the treatment of the B cell lymphomas.

By constructing a bispecific antibody, it is possible to recruit myeloid effector cells which express markers such as CD3 while targeting tumor cells, thereby achieving the purpose of killing the tumor cells more effectively.

In addition to immunotherapy of a tumor, the bispecific antibody can also be used in the treatment of other diseases, which for example, by targeting viral antigens and CD3, can direct T cells to kill viruses, so as to allow the treatment of viral infections or diseases caused by viruses. Depending on the nature of the target, the bispecific antibody can have different functions to achieve the goal of treating different diseases.

Although researchers have already designed a variety of bispecific antibodies, they still did not meet the needs of drug development. The main content of the present invention is to design a novel bispecific antibody, which has an asymmetric structure and is therefore referred to as an asymmetric bispecific antibody (AsBs Ab), which has a long half-life in vivo and can have a better expression from cells, and more importantly, which can monovalently bind to an immune effector cell, that is, one antibody molecule only binds to an epitope on one immune effector cell, and can prevent mutual killing due to the coupling between immune effector cells.

The present invention provides an asymmetric bispecific antibody comprising:

a first chain comprising, in order from the N-terminus to the C-terminus, a light chain variable region (VL) and a light chain constant region (CL);

a second chain comprising, in order from the N-terminus to the C-terminus, a heavy chain variable region, a heavy chain constant region, and a single-chain variable fragment (scFv), wherein the VL and CL of the first chain and a heavy chain VH and CH1 of the second chain together constitute an antigen-binding fragment (Fab) against a first antigen or epitope; the heavy chain constant region of the second chain comprises the CH1 domain and a Fc region of an antibody heavy chain; the scFv region of the second chain comprises, in order from the N-terminus to the C-terminus, a heavy chain variable region and a light chain variable region against a second antigen or epitope, or in order from the N-terminus to the C-terminus, a light chain variable region and a heavy chain variable region against a second antigen or epitope; and a third chain comprising a heavy chain Fc region of the third chain, wherein the heavy chain Fc region of the third chain comprises an antibody hinge region, CH2 and CH3.

In particular, the second chain comprises a hinge region positioned between the CH1 domain and the Fc region, and the third chain comprises, in order from the N-terminus to the C-terminus, the hinge region and the heavy chain Fc region of the third chain.

In particular, the third chain comprises a hinge region, a CH2 domain, and a CH3 domain.

In particular, the terminus of the light chain constant region of the first chain is linked to the terminus of the heavy chain constant region of the second chain by a disulfide bond.

In particular, there is a disulfide bond between the hinge region of the second chain and the hinge region of the third chain, such as those found in natural antibodies.

In particular, the light chain constant region of the first chain is linked to the heavy chain constant region of the second chain by a disulfide bond, and/or 0, 1 or 2 disulfide bond(s) is (are) provided between the CH3 domain of the second chain and the CH3 domain of the third chain, preferably wherein the disulfide bond(s) is (are) introduced by introducing cysteine at corresponding positions in the second heavy chain variable region of the second chain and the light chain variable region of the second chain and/or the CH3 domain of the second chain and the CH3 domain of the third chain.

In order to prepare such a bispecific antibody, a ternary-vector antibody expression system is designed. In this system, the bispecific antibody is composed of three polypeptide chains, wherein a first polypeptide chain is an antibody light chain having intact sequences of a variable region and a constant region of an antibody; a second polypeptide chain is an fusion protein chain of an intact antibody heavy chain and another single chain antibody (scFv), which chain comprises, in order from the N-terminus to the C-terminus, a heavy chain variable region, a heavy chain constant region, and a SCFV of another antibody; and a third polypeptide chain only comprises a heavy chain hinge region and a Fc fragment. During intracellular expression of these three polypeptide chains, the first polypeptide chain (the light chain of a first antibody) is paired with the N-terminus of the second polypeptide chain (the heavy chain of the first antibody) to form an antibody Fab structure which can bind to an antigen epitope; the C-terminus of the second polypeptide chain comprises a scFv of an antibody, which can bind to another antigen epitope; a disulfide bond is formed in the hinge regions of the third polypeptide chain and the second polypeptide chain, forming a Fc dimer. In this way, such a bispecific antibody molecule is an asymmetrically structured molecule having three chains, which binds to an antigen via the Fab fragment at the N-terminus and further binds to another antigen via the scFv at the C-terminus, achieving the purpose of the bispecific antibody.

The bispecific antibody designed in the present invention is characterized by an asymmetric structure of the Fc in the antibody. This bispecific antibody comprises two Fc-containing protein chains, wherein one Fc-containing protein chain is long, and comprises starting from the N-terminus: (1) a heavy chain variable region and a heavy chain CH1 of a first antibody, (2) a Fc region (a hinge region, CH2, and CH3), (3) a scFv of another antibody at the C-terminus, which for example, in one embodiment, has a molecular weight of about 77 kD; and the other Fc-containing protein chain is a Fc containing a hinge region, which for example, in one embodiment, has a molecular weight of 29 kD. In order to achieve heterologous pairing of the long-chain Fc and the short-chain Fc, a hole-knob pairing structure is designed between the two Fc sequences, which by amino acid mutations in the Fc region, reduces the formation of a homodimer Fc, and increases the heterologous pairing of the long-chain Fc and the short-chain Fc, thereby achieving the purpose of a monovalent and bispecific function. Since the two polypeptides containing a Fc fragment have greatly different molecular weights, even if a small amount of Fcs form a homodimer, the homodimer can be removed by subsequent purification.

The basic structure of the asymmetric bispecific antibody of the present invention can be seen in FIG. 1. This structure can be used to express bispecific antibodies for a variety of different purposes. In such a structure of the bispecific antibody, two antigen-binding regions, that is, a Fab and scFv, bind to different antigens, in which the Fab can bind to a tumor antigen, can bind to an immune effector cell surface antigen, and can also bind to another antigen epitope; and the scFv can bind to a tumor antigen, can bind to an immune effector cell surface antigen, and can also bind to another antigen epitope. The antibody of the present invention has a structure especially useful for the treatment of a tumor/cancer, such as a B cell associated tumor, etc. When the Fab and scFv of such a bispecific antibody bind to a tumor antigen and an immune effector cell surface antigen, respectively, the immune effector cell can be coupled to the tumor cell, thereby killing the tumor cell and achieving an immunotherapic effect.

The tumor antigen which can be used in the present invention includes, but is not limited to AFP, BCMA, CEA, Claudin, CA19-9, CA125, DR5, EMP2, GPA33, EGFR, Folate, HER2, HER3, FGFR1, c-MET, PDGFR, VEGFR, CD16, CD19, CD20, CD22, CD25, CD30, CD33, CD38, CD45, CD47, CD123, CD133, CD137, CD138, PSMA, TAG72, Tim-3, Trop-2, P-cadherin, gp100, PD-L1, and EpCAM.

There are also various effector cell surface antigens that can be used for the bispecific antibody described in the present invention, including but not limited to: FcγRI (CD64), FcγRIIA (CD32), FcγRIIB (CD32), FcγRIIIA (CD16a), FcγRIIIB (CD16b), FcαRI (CD89), CD3, and PD1. Commonly used are T lymphocytes, for which CD3 is used as an optional cell surface marker, and other T cell surface markers are also possible. In addition to T cells, many other cells also have immune effects, such as neutrophils, monocytes, etc., which can also be bound with different cell markers. Especially, it is particular that CD89 is a surface marker which is expressed on neutrophils and monocytes. Among the bispecific antibodies of the present invention, an example is a bispecific antibody which can allow the effector cell to kill a CD19-positive cell, including a CD19-positive tumor cell, by targeting CD89 on the one hand and targeting CD19 on the other hand.

In addition, it should be noted that the bispecific antibody of the present invention can also bind to two tumor antigens, which binds to two target molecules respectively, or binds to different epitopes of the same target molecule, to thereby achieve blocking of tumor signals, or killing of tumor cells by other mechanisms. Further, the bispecific antibody of the present invention can also be used for the treatment of diseases other than tumors, for example, by simultaneously binding to two non-tumor related targets to realize its biological function according to the mechanism of action. The bispecific antibodies having such structures or functions are all within the application scope of the inventive technology.

A vector encoding the bispecific antibody having the above three polypeptide chains can be constructed by gene cloning, and the vector can be a plasmid, a virus, a DNA fragment or the like, and can be produced by conventional molecular biotechnology. A commonly used method is a method in which the three polypeptide chains can be synthesized by PCR amplification and cloned into a bacterial plasmid. Many plasmids, such as pcDNA3.1 etc., can be used for this purpose. The plasmid is subjected to gene sequencing and then can be used for cell transfection to allow expression. A variety of cells can be used to express the bispecific antibody of the present invention, such as a mammalian cell, an insect cell, a yeast cell, a bacterial cell, and the like. A CHO cell (Chinese hamster ovary cell) is a commonly used mammalian cell, and the expression can also be carried out using a HEK293 cell, a myeloma cell, and the like. The bispecific antibody of the present invention involves three polypeptide chains which can be cloned into one, two, or three vectors to be expressed. Taking the HEK293 cell as an example, DNAs encoding the three polypeptides can be cloned into three plasmids respectively, and the three plasmids are separately purified and transfected into a cell by co-transfection. The transfection method can be carried out using a DNA transfection kit. The transfection method is classified into transient transfection and stable transfection. The transient transfection can produce a relatively small amount of proteins in a short period of time, while the stable transfection can produce a stable cell line and can achieve a large-scale protein expression.

DETAILED DESCRIPTION OF EMBODIMENTS

Figure 1:
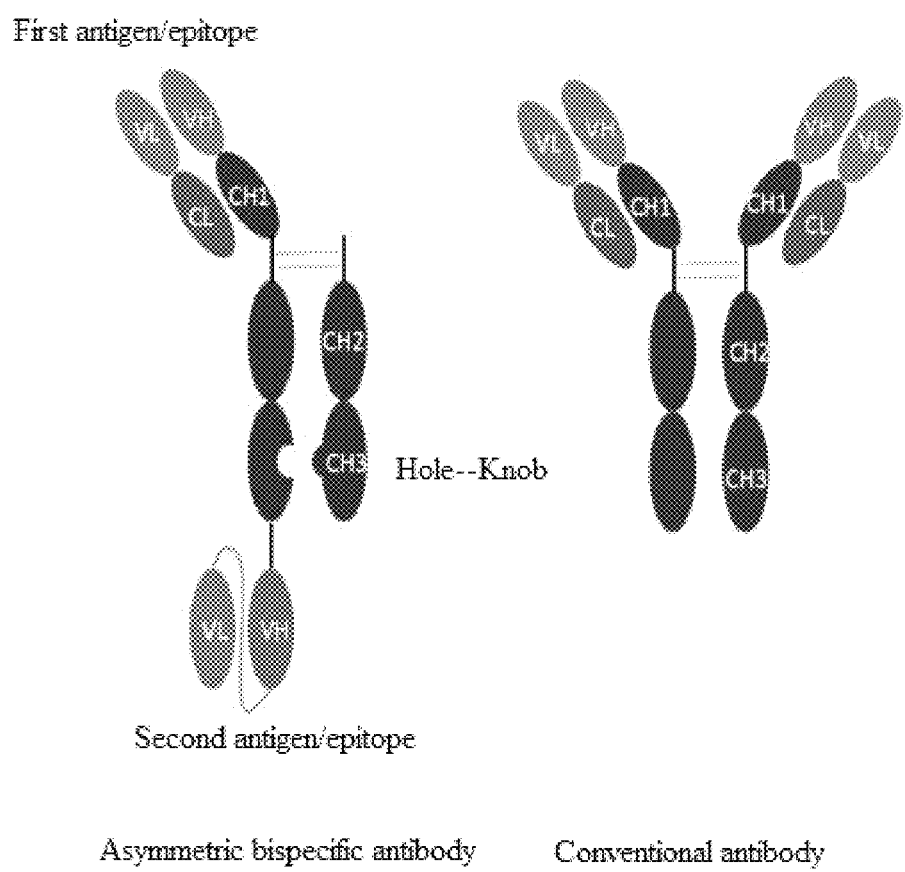
FIG. 1 shows an exemplary structure diagram of an asymmetric bispecific antibody of the present invention, which figure includes both an asymmetric bispecific antibody of the present invention and an antibody of a normal form.

The present invention provides an asymmetric bispecific antibody comprising:

a first chain comprising, in order from the N-terminus to the C-terminus, a light chain variable region (VL) and a light chain constant region (CL);

a second chain comprising, in order from the N-terminus to the C-terminus, a heavy chain variable region, a heavy chain constant region, and a single chain antibody (scFv) sequence, wherein the VL and CL of the first chain and a heavy chain VH and CH1 of the second chain together constitute an antigen-binding fragment (Fab) of a first antibody; the heavy chain constant region of the second chain comprises the CH1 domain and a Fc region of an antibody heavy chain; the scFv region of the second chain comprises, in order from the N-terminus to the C-terminus, a heavy chain variable region and a light chain variable region of a second antibody, which are linked via an appropriate linking sequence; or in order from the N-terminus to the C-terminus, a light chain variable region and a heavy chain variable region of a second antibody, which are linked via an appropriate linking sequence; and a third chain comprising a heavy chain Fc region of the third chain, wherein the heavy chain Fc region of the third chain comprises a CH2 domain and a CH3 domain of the third chain.

In some specific embodiments, an interface in contact with the CH3 domain of the second chain and the CH3 domain of the third chain is subjected to a modification to reduce the formation of a homodimer, wherein the modification is:

a) substitution of an amino acid residue at the above interface in the CH3 domain of the second chain with an amino acid residue having a large side chain volume, thereby generating a knob on one side of the second chain at the interface, and b) substitution of an amino acid residue at the above interface in the CH3 domain of the third chain with an amino acid residue having a small side chain volume, thereby generating a hole on one side of the third chain at the interface, wherein the knob is positioned in the hole.

In some specific embodiments, the amino acid residue having a large side chain volume is selected from the group consisting of: arginine (R), phenylalanine (F), tyrosine (Y), and tryptophan (W). Preferably, the substitution of an amino acid residue at the above interface in the CH3 domain of the second chain with an amino acid residue having a large side chain volume is a T366W mutation (corresponding to the amino acid at position 146 in SEQ ID NO: 5 of the present application).

In some specific embodiments, the amino acid residue having a small side chain volume is selected from the group consisting of: alanine (A), serine (S), threonine (T), and proline (V). Preferably, the substitution of an amino acid residue at the above interface in the CH3 domain of the second chain with an amino acid residue having a small side chain volume is T366S, L368A and Y407V mutations (corresponding to the amino acids at positions 146, 148 and 187 in SEQ ID NO: 4 of the present application).

In some specific embodiments, 1, 2 or 3 disulfide bonds are provided between the hinge region of the second chain and the hinge region of the third chain.

If the Fc sequence used in the bispecific antibody has a property of binding to FcγR of the natural Fc, it may allow the effector cells such as NK to bind to the bispecific antibody and induce an ADCC effect. Such an ADCC effect may enhance the ability of the bispecific antibody to kill tumor cells by binding the bispecific antibody to the tumor target, but it is also likely to kill effector cells such as CD3 by binding the bispecific antibody to an effector cell target, resulting in an reduced anti-tumor effect. In some specific embodiments, in order to prevent the influence of ADCC on the efficacy of the bispecific antibody, the Fc region of the second chain and the heavy chain Fc region of the third chain are further modified to eliminate the antibody-dependent cell-mediated cytotoxicity (ADCC), such as mutation of Asn at position 297 to Ala.

In some specific embodiments, the light chain variable region of the first chain and the heavy chain variable region of the second chain are capable of specifically binding to a first antigen or epitope.

In some specific embodiments, the scFv region of the second chain is capable of specifically binding to a second antigen or epitope.

In some specific embodiments, the first antigen or epitope is different from the second antigen or epitope. In other specific embodiments, the first antigen or epitope is the same as the second antigen or epitope.

In some specific embodiments, the first antigen or epitope is a surface antigen or epitope of a tumor cell and the second antigen or epitope is a surface antigen or epitope of an immune effector cell. In other specific embodiments, the first antigen or epitope is a surface antigen or epitope of an immune effector cell and the second antigen or epitope is a surface antigen or epitope of a tumor cell. In still other specific embodiments, the first antigen or epitope is a surface antigen or epitope of a tumor cell and the second antigen or epitope is another surface antigen or epitope of a tumor cell.

In particular, the surface antigen or epitope of a tumor cell is selected from the group consisting of: AFP, BCMA, CA19-9, CA125, CEA, Claudin, DR5, EMP2, GPA33, EGFR, Folate, HER2, HER3, FGFR1, c-MET, PDGFR, VEGFR, CD16, CD19, CD20, CD22, CD25, CD30, CD33, CD38, CD45, CD47, CD123, CD133, CD137, CD138, PSMA, TAG72, Tim-3, Trop-2, P-cadherin, gp100, PD-L1, and EpCAM.

In particular, the surface antigen or epitope of an immune effector cell may be selected from the group consisting of: FcγRI (CD64), FcγRIIA (CD32), FcγRIIB (CD32), FcγRIIIA (CD16a), FcγRIIIB (CD16b), FcαRI (CD89), CD3, and PD1.

In some specific embodiments, each of the moieties in the antibody of the present invention, including but not limited to the VL region, the CL region of the first chain; the heavy chain VH region, the heavy chain constant region (including the CH1 region, hinge region, CH2 region and CH3 region) and the scFv region, of the second chain; the heavy chain Fc region (including the hinge region, CH2 region and CH3 region) of the third chain, can be independently derived from human, mice, rats, rabbits, or camelid species, etc. Preferably, the CL region of the first chain, the heavy chain constant region of the second chain, and the heavy chain Fc region of the third chain are all derived from human.

In some specific embodiments, the present invention provides an anti-CD89/CD20 bispecific antibody, wherein the first antigen or epitope is CD89 and the second antigen or epitope is CD20, or the first antigen or epitope is CD20 and the second antigen or epitope is CD89. Preferably, the first chain has a sequence of SEQ ID NO: 1; the VH and CH1 of the second chain have a sequence of SEQ ID No: 2, the scFv region of the second chain has a sequence of SEQ ID No: 3, and one of the Fc region of the second chain and the Fc region of the third chain has a sequence of SEQ ID No: 4 or 49 and the other has a sequence of SEQ ID No: 5 or 50. In particular, the Fc region of the second chain has a sequence of SEQ ID No: 4, and the Fc region of the third chain has a sequence of SEQ ID No: 5. In particular, the Fc region of the second chain has a sequence of SEQ ID No: 49, and the Fc region of the third chain has a sequence of SEQ ID No: 50.

In some specific embodiments, the present invention provides an anti-CD19/CD3 bispecific antibody, wherein the first antigen or epitope is CD19 and the second antigen or epitope is CD3, or the first antigen or epitope is CD3 and the second antigen or epitope is CD19. Preferably, the first chain has a sequence of SEQ ID NO: 6; the VH and CH1 of the second chain have a sequence of SEQ ID No: 7, the scFv region of the second chain has a sequence of SEQ ID No: 8, and one of the Fc region of the second chain and the Fc region of the third chain has a sequence of SEQ ID No: 4 or 49 and the other has a sequence of SEQ ID No: 5 or 50. In particular, the Fc region of the second chain has a sequence of SEQ ID No: 4, and the Fc region of the third chain has a sequence of SEQ ID No: 5. In particular, the Fc region of the second chain has a sequence of SEQ ID No: 49, and the Fc region of the third chain has a sequence of SEQ ID No: 50.

In some specific embodiments, the Fc region of the second chain is linked to the scFv region by a peptide linker, preferably the peptide linker being 0, 1, 2, or 3 GGGGSs.

In some specific embodiments, the light chain variable region in the scFv region of the second chain is linked to the heavy chain variable region thereof by a peptide linker, preferably the peptide linker being 0, 1, 2, or 3 GGGGSs.

In some specific embodiments, the first antigen or epitope in the antibody of the present invention is CD89, and the VL of the first chain comprises the following CDRs: CDR1 having a sequence as set forth in SEQ ID NO: 9, CDR2 having a sequence as set forth in SEQ ID NO: 10, and CDR3 having a sequence as set forth in SEQ ID NO: 11; and the VH of the second chain comprises the following CDRs: CDR1 having a sequence as set forth in SEQ ID NO: 12, CDR2 having a sequence as set forth in SEQ ID NO: 13, and CDR3 having a sequence as set forth in SEQ ID NO: 14.

In some specific embodiments, the first antigen or epitope in the antibody of the present invention is CD19, and the VL of the first chain comprises the following CDRs: CDR1 having a sequence as set forth in SEQ ID NO: 15, CDR2 having a sequence as set forth in SEQ ID NO: 16, and CDR3 having a sequence as set forth in SEQ ID NO: 17; and the VH of the second chain comprises the following CDRs: CDR1 having a sequence as set forth in SEQ ID NO: 18, CDR2 having a sequence as set forth in SEQ ID NO: 19, and CDR3 having a sequence as set forth in SEQ ID NO: 20.

In some specific embodiments, the second antigen or epitope in the antibody of the present invention is CD20, and the scFv of the second chain has a sequence as set forth in SEQ ID No: 3.

In some specific embodiments, the second antigen or epitope in the antibody of the present invention is CD3, and the scFv of the second chain has a sequence as set forth in SEQ ID No: 8.

In another aspect, the present invention provides a method for preparing the antibody of the present invention, comprising the steps of:
a) transforming a host cell with
a first vector comprising a nucleic acid molecule encoding the first chain,
a second vector comprising a nucleic acid molecule encoding the second chain, and
a third vector comprising a nucleic acid molecule encoding the third chain;
b) culturing the host cell under conditions allowing the synthesis of the antibody; and
c) recovering the antibody from the culture.

In some embodiments, the first vector, the second vector and the third vector are different vectors. In some embodiments, the first vector, the second vector and the third vector are the same vector.

In another aspect, the present invention provides a method for preparing the antibody of the present invention, comprising the steps of:
a) transforming a host cell with
a vector comprising a nucleic acid sequence encoding the first chain, a nucleic acid sequence encoding the second chain, and a nucleic acid sequence encoding the third chain;
b) culturing the host cell under conditions allowing the synthesis of the antibody; and
c) recovering the antibody from the culture.

In yet another aspect, the present invention provides a host cell comprising:
a first vector comprising a nucleic acid molecule encoding the first chain,
a second vector comprising a nucleic acid molecule encoding the second chain, and
a third vector comprising a nucleic acid molecule encoding the third chain.

In yet another aspect, the present invention provides a host cell comprising:
a vector comprising a nucleic acid sequence encoding the first chain, a nucleic acid sequence encoding the second chain, and a nucleic acid sequence encoding the third chain.

In some embodiments of the present invention, the vector is an expression vector, preferably a plasmid, a virus or other vectors.

In some embodiments of the present invention, the host cell is a prokaryotic cell or a eukaryotic cell. In particular, the prokaryotic host cell may be *Escherichia coli, Bacillus subtilis, Streptomyces* or *Proteus Mirabilis* and the like. The eukaryotic host cell may be a fungus such as *Pichia pastoris, Saccharomyces cerevisiae, Schizosaccharomyces, Trichoderma;* an insect cell such as a grass armyworm cell; a plant cell such as a tobacco cell; a mammalian cell such as a 293 cell, 293F cell, CHO cell, NSO cell, BHK cell, COS cell and myeloma cell, etc. In some embodiments, the host cell of the present invention is preferably a mammalian cell, more preferably a BHK cell, a CHO cell, a NSO cell or a COS cell.

In yet another aspect, the present invention provides an antibody capable of specifically binding to CD89, wherein the antibody comprises: a heavy chain CDR1, a heavy chain CDR2, a heavy chain CDR3, a light chain CDR1, a light chain CDR2, and a light chain CDR3, wherein
the heavy chain CDR1 has an amino acid sequence as set forth in SEQ ID NO: 12,
the heavy chain CDR2 has an amino acid sequence as set forth in SEQ ID NO: 13,
the heavy chain CDR3 has an amino acid sequence as set forth in SEQ ID NO: 14,
the light chain CDR1 has an amino acid sequence as set forth in SEQ ID NO: 9,
the light chain CDR2 has an amino acid sequence as set forth in SEQ ID NO: 10, and
the light chain CDR3 has an amino acid sequence as set forth in SEQ ID NO: 11.

In some embodiments, the anti-CD89 antibody of the present invention comprises a heavy chain variable region having an amino acid sequence as set forth in SEQ ID NO: 23, and a light chain variable region having an amino acid sequence as set forth in SEQ ID NO:24.

In yet another aspect, the present invention provides an antibody capable of specifically binding to CD19, wherein the antibody comprises: a heavy chain CDR1, a heavy chain CDR2, a heavy chain CDR3, a light chain CDR1, a light chain CDR2, and a light chain CDR3, wherein
the heavy chain CDR1 has an amino acid sequence as set forth in SEQ ID NO: 18,
the heavy chain CDR2 has an amino acid sequence as set forth in SEQ ID NO: 19,
the heavy chain CDR3 has an amino acid sequence as set forth in SEQ ID NO: 20,
the light chain CDR1 has an amino acid sequence as set forth in SEQ ID NO: 15,
the light chain CDR2 has an amino acid sequence as set forth in SEQ ID NO: 16, and
the light chain CDR3 has an amino acid sequence as set forth in SEQ ID NO: 17.

In some embodiments, the anti-CD19 antibody of the present invention comprises a heavy chain variable region having an amino acid sequence as set forth in SEQ ID NO: 38, and a light chain variable region having an amino acid sequence as set forth in SEQ ID NO: 37.

In yet another aspect, the present invention provides a pharmaceutical composition comprising the antibody of the present invention, and at least one pharmaceutically acceptable excipient.

In yet another aspect, the present invention provides use of the antibody of the present invention in the preparation of a medicament for the treatment of a disease.

In yet another aspect, the present invention provides an asymmetric bispecific antibody as described above for use in the treatment of a disease.

In yet another aspect, the present invention provides a method for treating a disease comprising: administering a therapeutically effective amount of the antibody of the present invention to a subject in need thereof.

In some embodiments, the disease is a cancer or tumor, preferably those in which a first antigen or epitope is expressed on the surface of a cancer cell or tumor cell, such as B lymphocyte tumors (such as non-Hodgkin's lymphoma), leukemia (e.g., chronic lymphocytic leukemia), lung cancer, gastric cancer, liver cancer, breast cancer, pancreatic cancer, prostate cancer, bladder cancer, head and neck cancer, and cervical cancer.

In some embodiments, the disease is a disease characterized by expression of B cells. In certain embodiments, the disease is non-responsive to the treatment with at least one of an anti-CD19 antibody and an anti-CD20 antibody.

In still other embodiments, the disease is an autoimmune disease. In particular, the autoimmune disease is one or more of multiple sclerosis, rheumatoid arthritis, systemic lupus erythematosus, psoriatic arthritis, psoriasis, vasculitis, IgA nephritis, uveitis, Crohn's disease, and type 1 diabete, etc.

Definitions

Unless defined otherwise, all technical and scientific terms used herein have the same meaning as commonly understood by those skilled in the art. With regard to the definitions and terms in the art, reference may be made to Current Protocols in Molecular Biology (Ausubel) by the skilled persons. The standard three- and/or one-letter code used for expressing one of 20 common L-amino acids in the art is adopted as the abbreviation of an amino acid residue.

Although the numerical ranges and approximate parameter values are shown in a broad range in the present invention, all the numerical values set forth in the specific examples are described as precisely as possible. However, any numerical value inherently contains certain errors necessarily resulting from the standard deviation found in their respective measurements. Additionally, all ranges disclosed herein are to be understood to encompass any and all subranges subsumed therein. For example, a stated range "1 to 10" as should be considered to include any and all subranges between (and inclusive of) the minimum value of 1 and the maximum value of 10; that is, all subranges beginning with a minimum value of 1 or more, such as 1 to 6.1, and ending with a maximum value of 10 or less, such as 5.5 to 10. Additionally, any reference referred to as being "incorporated herein" is to be understood as being incorporated in its entirety.

Additionally, it should be noted that, as used in the present invention, the singular form includes the plural referent, unless the context explicitly and clearly indicates as limiting to one stated referent. The term "or" and the term "and/or" are used interchangeably, unless otherwise clearly indicated in the context.

As used herein, the term "asymmetric" means that the antibody of the present invention cannot be separated into two moieties that are symmetrical to each other. Specifically, some natural antibodies (e.g., IgG) comprise two identical heavy chains and two identical light chains, wherein a moiety consisting of one heavy chain and one light chain is symmetrical to the other moiety consisting of another heavy chain and another light chain. Preferably, the asymmetric antibody of the present invention is a heterotrimer consisting of three different chains.

As used herein, the term "bispecific" is intended to encompass any agent having two different binding specificities, for example, a heteromultimer, a monomer, a protein, a peptide, or a protein or peptide complex, preferably an antibody.

As used herein, the term "antibody" encompasses full length antibodies (e.g., IgG1 or IgG4 antibodies), various functional fragments thereof (e.g., those which may comprise only antigen-binding moieties, such as Fab, F(ab')$_2$ or scFv fragments), as well as modified antibodies (e.g., humanized, glycosylated, etc.). In some applications, a modification is performed to remove undesired glycosylation sites, or to have no fucose moiety on the oligosaccharide chain to for example, enhance antibodies having an antibody-dependent cellular cytotoxicity (ADCC) function. In other applications, a galactosylation modification can be made to alter the complement dependent cytotoxicity (CDC).

As used herein, the term "functional fragment" is intended to refer to a fragment retaining the function of a full-length antibody, such as an antigen-binding fragment, and particularly refer to an antibody fragment such as a Fv, scFv (sc refers to single chain), Fab, F(ab')$_2$, Fab', scFv-Fc fragment or diabody, or any fragment which is capable of increasing the half-life by a chemical modification or by incorporation into liposomes, the chemical modification including for example, addition of a poly(alkylene) glycol such as polyethylene glycol (i.e., "polyethylene glycolylated, PEGylated") (a PEGylated fragment being referred to as Fv-PEG, scFv-PEG, Fab-PEG, F(ab')$_2$-PEG or Fab'-PEG, in which "PEG" is polyethylene glycol).

As used herein, the term "CDR region" or "CDR" refers to a hypervariable region of the heavy and light chains of an immunoglobulin, as defined by Kabat et al. (Kabat et al., Sequences of proteins of immunological interest, 5th Ed., U.S. Department of Health and Human Services, NIH, 1991, and later versions). There are three heavy chain CDRs and three light chain CDRs. The term CDR or CDRs is used herein to indicate, according to the case, one of these regions or several, or even the whole, of these regions which contain the majority of the amino acid residues responsible for the binding by affinity of the antibody for the antigen or the epitope which it recognizes.

As used herein, the term "Fc region" or "Fc moiety" is a term well known to those skilled in the art and is defined based on antibody cleavage by papain. The Fc moiety of the antibody is directly involved in complement activation, C1q binding, C3 activation and Fc receptor binding. Although the influence of an antibody on the complement system depends on specific conditions, binding to C1q is resulted from the binding sites identified in the Fc moiety. Such binding sites are known in the prior art and described for example, in Lukas, T. J., et al., J. Immunol. 127 (1981) 2555-2560; Jrunhouse, R., and Cebra, J. J., Mol. Immunol. 16 (1979) 907-917; Burton, D. R. et al., Nature 288 (1980) 338-344; Thommesen, J. E. et al., Mol. Immunol. 37 (2000) 995-1004; Idusogie, E. E., et al., J. Immunol. 164 (2000) 4178-4184; Hezareh, M. et al., J. Virol. 75 (2001) 12161-12168; Morgan, A. et al., Immunology 86 (1995) 319-324; and EP 0 307 434. The binding sites are, for example, L234, L235, D270, N297, E318, K320, K322, P331 and P329 (numbering according to the EU index in Kabat, see below). Antibodies of subtypes IgG1, IgG2 and IgG3 typically exhibit complement activation, C1q binding and C3 activation, whereas IgG4 does not activate the complement system, does not bind C1q and does not activate C3. Preferably, the Fc moiety is a human Fc moiety.

As used herein, the term "Fab region" refers to VH and CH1 domains of the heavy chain ("Fab heavy chain"), or VL and CL domains of a light chain ("Fab light chain") of an immunoglobulin, or both thereof.

As used herein, the term "scFv" or "single chain antibody fragment" refers to a single chain consisting of a heavy chain variable region and a light chain variable region of an antibody being linearly linked together by a linker (e.g., a short peptide of 10~25 amino acids), which exhibits specific binding to an antigen.

As used in the present invention, the term "peptide linker" refers to a peptide for linking different antigen binding sites and/or antibody fragments ultimately comprising different antigen binding sites (e.g., a single chain Fv, a full length antibody, a VH domain, and/or VL domain, Fab, (Fab)$_2$ and Fc moieties) together, which preferably has a synthetically derived amino acid sequence. The peptide linker may comprise one or more of the amino acid sequences set forth in Table 1 below, as well as other optional amino acids.

As used herein, the term "binding" or "specifically binding" refers to the binding of an antibody to an antigen epitope in an in vitro assay, preferably in a cell-based ELISA using CHO cells which express wild-type antigens. Binding refers to a binding affinity of $10^{-8}$ M or lower, preferably of $10^{-13}$ to $10^{-9}$ M (KD). The binding of an antibody to an antigen or FcγRIII can be studied by BIAcore assay (Pharmacia Biosensor AB, Uppsala, Sweden). The binding affinity is defined by the terms ka (binding rate constant of an antibody in an antibody/antigen complex), kD (dissociation constant) and KD (kD/ka).

As used herein, "therapeutically effective amount" or "effective amount" refers to a dose that is sufficient to demonstrate a benefit to the subject to which it is administered. The actual amount administered, as well as the rate and time-course of administration, will depend on the condition and severity of the subject being treated. Prescription of treatment, e.g., decisions on dosage, etc., is ultimately within the responsibility of general practitioners and other medical doctors and relies on decisions of them, and typically takes account of the disease being treated, the condition of the individual patient, the site of delivery, the method of administration, and other factors known to physicians.

As used herein, the term "subject" refers to mammals, such as humans, and can also be other animals, such as wild animals (such as herons, cranes, cranes, etc.), livestock (such as ducks, geese, etc.) or experimental animals (such as orangutans, monkeys, rats, mice, rabbits, guinea pigs, woodchucks, ground squirrels, etc.).

The composition of the present invention can be administered by a variety of methods known in the art. As will be appreciated by the skilled artisan, the route and/or mode of administration will vary depending upon the desired results. In order to administer a compound of the present invention by a certain route of administration, it may be necessary to coat the compound with, or to co-administer the compound with, a material to prevent its inactivation. For example, the compound can be administered to a subject in an appropriate carrier, for example liposomes, or a diluent. The pharmaceutically acceptable diluent includes a saline solution and an aqueous buffer solution. The pharmaceutically acceptable carrier includes a sterile aqueous solution or dispersion and sterile powder for the extemporaneous preparation of a sterile injectable solution or dispersion. The use of such media and agents for pharmaceutically active substances is known in the art.

As used herein, the phrases "parenteral administration" and "administered parenterally" mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, and intrasternal injections and infusions.

The composition of the present invention may also comprise adjuvants such as preservatives, wetting agents, emulsifying agents and dispersing agents. The presence of microorganisms can be avoided by the sterilization procedure described above together with by the inclusion of various antibacterial and antifungal agents, for example, parabens, chlorobutanol, phenol, sorbic acid, and the like. It may also be desirable to include isotonic agents, such as sugars, sodium chloride, and the like, in the composition. In addition, prolonged absorption of the injectable pharmaceutical form may be brought about by the inclusion of an agent which delays absorption, such as aluminum monostearate and gelatin.

Regardless of the route of administration selected, the compounds of the present invention, which may be used in a suitable hydrated form, and/or the pharmaceutical compositions of the present invention are formulated into pharmaceutically acceptable dosage forms by conventional methods known to those skilled in the art.

The bispecific antibody of the present invention contains an Fc fragment, and such a protein can be isolated and purified by protein An affinity chromatography after being expressed in cells, which is one of the advantages of the bispecific antibody of the present invention. After the affinity chromatography, the protein can be further purified by ion exchange, molecular sieve, hydrophobic chromatography or the like. The purity of the bispecific antibody can be identified by polyacrylamide gel electrophoresis, HPLC or the like. The protein of interest has a molecular weight of about 133 kD.

The inventors have surprisingly found that as compared with other bispecific antibodies, the asymmetric bispecific antibody of the present invention exhibits particularly superior performances, which include but are not limited to: each of the two different specificities being monovalently binding (i.e., one antibody molecule binds only to one antigen epitope, such as an epitope on an immune effector cell, which allows to prevent mutual killing due to coupling between immune effector cells); high level expression in cells; a longer half-life in vivo; higher biological activities; being more effective in killing tumor cells (such as B cells); being more effective in recruitment of immune effector cells (such as T cells and/or B cells); and less side effects.

In particular, the structure of the antibody of the present invention exhibits more superior performances than a bispecific T cell recruitment (BiTE) type of bispecific antibodies that are of interest in the bispecific antibody technology, e.g., Blinatumomab.

In order to construct a bispecific antibody with CD89-positive cells as immune effector cells, the inventors have first prepared an anti-CD89 monoclonal antibody. Such an antibody is obtained by conventional hybridoma technology, followed by gene cloning of the antibody to confirm the DNA sequences of the heavy and light chain variable regions of the antibody, thereby obtaining the amino acid sequences of the heavy and light chain variable regions of the antibody (as set forth in SEQ ID NOs: 21, 22, 23, 24, respectively). Thereafter, on this basis, the present inventors have constructed a bispecific antibody having a BiTE structure (an anti-CD20/CD89 bispecific antibody) and an asymmetric bispecific antibody having a structure of the present invention, respectively, wherein the sequence of Rituxan is used as the CD20 antibody, and a linking sequence that is identical to that in Blinatumomab is also used between two scFvs. As a result, it is found that the anti-CD20/CD89 bispecific antibody having a BiTE structure is not expressed or has a extremely low expression, in either HEK293 cells or CHO cells, resulting in that it is difficult to perform further experiments. Even if many different linking sequences and transfection methods have been tried, a desired expression level cannot be obtained. In contrast, the asymmetric bispecific antibody of the present invention can be well expressed in HEK293 and CHO cells, and has good biological activities. It is important that the antibody of the present invention has a more superior half-life in vivo.

In order to test the versatility of this novel bispecific antibody, a bispecific antibody targeting CD19 and CD3 is further constructed, which adopts an anti-CD19Fab/CD3 scFv structure. It is found that the bispecific antibody having this structure can also be well expressed in 293 cells and CHO cells, and thus demonstrated that the asymmetric bispecific antibody of the present invention is characterized by ease of expression. Furthermore, it is found that, as compared with the anti-CD19 scFv/CD3 scFv bispecific antibody (i.e., BiTE), the AsBs Ab created by the inventors is characterized not only by ease of expression, but also by a longer half-life and ease of purification. At the same time, the advantage that the BiTE monovalently binds to an immune effector cell and a tumor cell is retained in AsBs Ab. Therefore, the AsBs Ab bispecific antibody has a molecular structure which can overcome the disadvantages of the BiTE and has a high application value.

The following examples are provided to demonstrate and further illustrate some preferred embodiments and aspects of the present invention, and should not be construed as limiting the scope thereof.

Examples

Example 1

Preparation of Anti-CD89 Monoclonal Antibody

In order to prepare a bispecific antibody with CD89 cells as immune effector cells, a monoclonal antibody having a high affinity to CD89 must be first obtained.

BALB/c mice (Shanghai Slac Laboratory Animal Center) were immunized with Human CD89 Recombinant Protein (Sino Biologicals), and spleen lymphocytes were taken from the immunized mice and fused with SP2/0 myeloma cells (ATCCs) to prepare a hybridoma. The fused cells were cloned and cultured in a 96-well cell culture plate, and detected for positive clones by using ELISA with CD89 coating. The positively cloned hybridoma cells were subjected to amplification culture and subcloning culture. Several hybridoma cell strains having anti-CD89 antibodies were thus obtained, which were confirmed to have a high affinity to CD89 by ELISA and flow cytometry, and were thus determined as a hybridoma cell strain having anti-CD89 monoclonal antibodies. Thereafter, DNA sequences (SEQ ID NOs: 21, 22) of heavy and light chain variable regions of the anti-CD89 antibody were obtained by cloning the antibody genes of the hybridoma cells, which were further used to obtain amino acid sequences (SEQ ID NOs: 23, 24) of the heavy and light chain variable regions. By sequence analysis, the sequences of six CDR regions of the light and heavy chains of the antibody (SEQ ID NOs: 9, 10, 11, 12, 13, 14) were determined.

Example 2

Construction of Anti-CD89/CD20 Asymmetric Bispecific Antibody

Among the three polypeptide chains of the constructed bispecific antibody, the first chain contained an anti-CD89 antibody VL and a human Kappa CL, in which the anti-CD89 antibody VL was amplified from the gene of the antibody obtained in Example 1 by PCR using anti-CD89 upstream and downstream primers (SEQ ID NOs: 25, 26), the human Kappa CL was amplified from a plasmid pFUSE2-CLIg-hK (Invivogen) by PCR using CL upstream and downstream primers (SEQ ID NOs: 27, 28), and then a complete anti-CD89 VL-CL chimeric light chain was synthesized by overlapping PCR and cloned into an expression plasmid pcDNA 3.1. The second polypeptide chain contained an anti-CD89 VH, a human IgG constant region, and an anti-CD20 scFv, in which the anti-CD89 antibody VH was amplified from the gene of the antibody obtained in Example 1 by PCR using corresponding upstream and downstream primers (SEQ ID NOs: 29, 30), the human IgG constant region was amplified from a relevant plasmid (pcDNA 3.1-hIgG1Fc-Hole, artificial gene synthesis, GENEWIZ, Suzhou, SEQ ID NO: 51) using upstream and downstream primers (SEQ ID NOs: 31, 32), which contained hole mutations in its Fc (T366S, L368A, and Y407V, corresponding to positions 146, 148 and 187 of SEQ ID NO: 4 in the present application), the anti-CD20 scFv was amplified from a relevant plasmid (pcDNA3.1-anti-CD20-scFv, artificial gene synthesis, GENEWIZ, Suzhou, SEQ ID NO: 52) using upstream and downstream primers (SEQ ID NOs: 33, 34), and finally a complete CD89 VH-human IgG CH (hole)-linking sequence $(G_4S)_3$-anti-CD20 scFv was synthesized by overlapping PCR and cloned into an expression plasmid pcDNA 3.1. The third chain was a human Fc containing a hinge region and contained a knob mutation (T366W, corresponding to position 146 of SEQ ID NO: 5 in the present application), which was amplified from a plasmid (pcDNA 3.1-hIgG1Fc-Knob, artificial gene synthesis, GENEWIZ, Suzhou, SEQ ID NO: 53) using upstream and downstream primers (SEQ ID NOs: 35, 36) and cloned into an expression vector pcDNA 3.1. The above three sequences of interest and vectors were respectively and sequentially added with two restriction sites AgeI and SalI. The expression vector was double digested with two enzymes, AgeI and SalI, and ligated with the DNA fragments obtained in the previous step in the designed sequence order according to a seamless cloning method. The fragments of interest were ligated to an eukaryotic expression vector pcDNA 3.1 by treating with a seamless cloning ligase kit (Vazyme). The ligated expression vector was transformed into DH5α competent cells, followed by picking and cloning, and then the plasmid was extracted and identified by enzyme digestion to select positive clones therefrom and screen the correct vector clones, thereby obtaining a vector capable of expressing the anti-CD89/CD20 asymmetric bispecific antibody.

Figure 2:
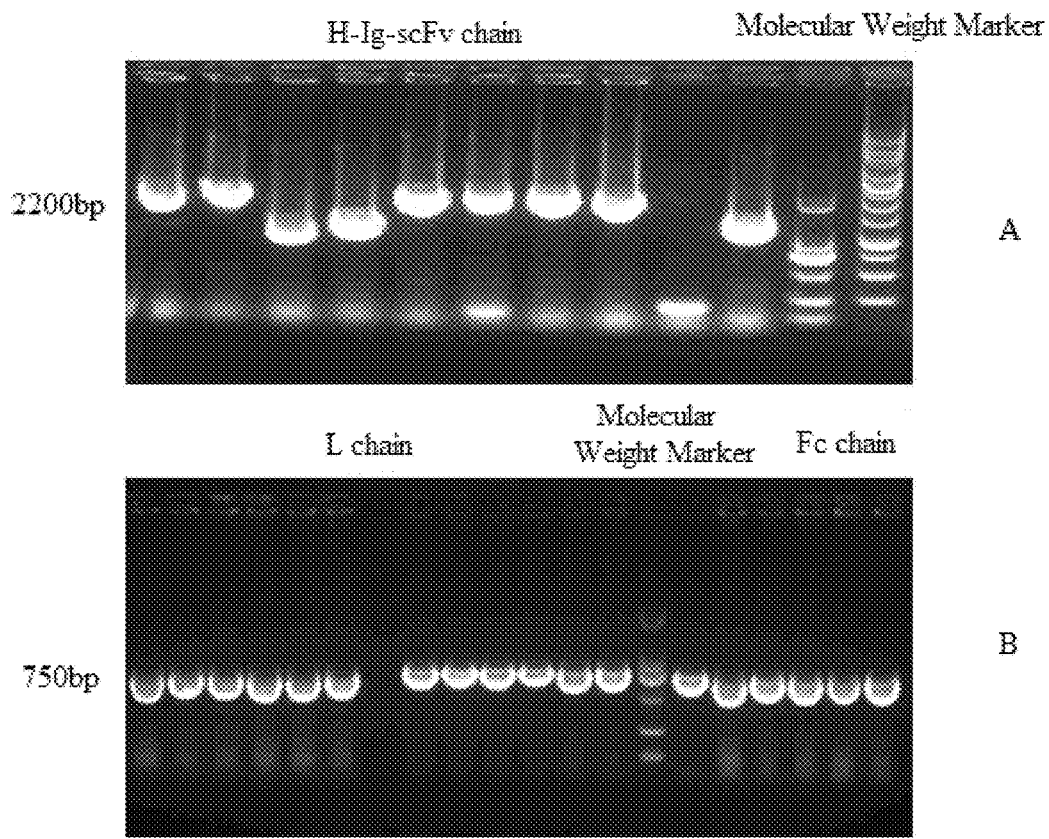
FIG. 2 shows an electrophoresis pattern of a gene of interest detected by colony PCR.

In addition, an anti-CD89/CD20 asymmetric bispecific antibody (CD89-CD20 mut) containing a mutation at position 297 in the Fc region (from Asn to Ala) was also constructed, in which the mutation was designed to allow the Fc region to lose the antibody-dependent cell-mediated cytotoxicity (ADCC). The recombinant plasmid obtained as described above was subjected to gene directed mutation, so as to mutate Asn at position 297 in the Fc regions of the two vectors, that is, the second chain heavy chain (hole) and the third chain Fc (knob) fragments, into Ala (corresponding to position 77 of SEQ ID NOs: 4 and 5 in the present application) to thereby lose the antibody-dependent cell-mediated cytotoxicity (ADCC) thereof. Thereafter, clones with correct DNA sequences were screened by PCR identification of the bacteria solution (as shown in FIG. 2) and then DNA sequencing.

Example 3

Construction of Anti-CD19/CD3 Asymmetric Bispecific Antibody

In this bispecific antibody, the Fab moiety was an anti-CD19 antibody, of which the antibody VL and VH sequences (SEQ ID NOs: 37, 38) were derived from a murine-derived anti-CD19 antibody which had been disclosed; and the scFv moiety was an anti-CD3 antibody, of which the svFV sequence (SEQ ID NO: 8) was derived from a scFv antibody which had been disclosed. The first polypeptide chain contained an anti-CD19 antibody VL and a human Kappa CL, in which the VL was amplified from a relevant plasmid (pcDNA 3.1-anti-CD19-scFv, artificial gene synthesis, GENEWIZ, Suzhou, SEQ ID NO: 54) by PCR using upstream and downstream primers (SEQ ID NOs: 39, 40), the human Kappa CL was obtained by PCR using CL upstream and downstream primers (SEQ ID NOs: 41, 42), and a complete anti-CD19 VL-CL chimeric light chain was synthesized by overlapping PCR and cloned into an expression plasmid pcDNA3.1. The second polypeptide chain contained an anti-CD19 VH, a human IgG constant region, and an anti-CD3 scFv, in which the anti-CD19 antibody VH was amplified from a relevant plasmid (pcDNA 3.1-anti-CD19-scFv, artificial gene synthesis, GENEWIZ, Suzhou, SEQ ID NO: 54) by PCR using corresponding upstream and downstream primers (SEQ ID NOs: 43, 44), the human IgG constant region was amplified from a relevant plasmid (pcDNA 3.1-hIgG1Fc-Hole, SEQ ID NO: 51) using upstream and downstream primers (SEQ ID NOs: 45, 46), which contained a hole mutation within its Fc, the anti-CD3 scFv was amplified from a relevant plasmid (pcDNA 3.1/CD3-scFv, artificial gene synthesis, GENEWIZ, Suzhou, SEQ ID NO: 55) using upstream and downstream primers (SEQ ID NOs: 47, 48), and a complete CD19 VH-human IgG CH (hole)-linking sequence $(G_45)_3$-anti-CD3 scFv was synthesized by overlapping PCR and cloned into an expression plasmid. The third chain was identical to that in Example 2. The sequences of interest were cloned into the expression plasmid by the same method as in Example 2, and DNA sequencing was performed to obtain clones having correct DNA sequences.

Example 4

Expression and Identification of Bispecific Antibodies

Figure 3:
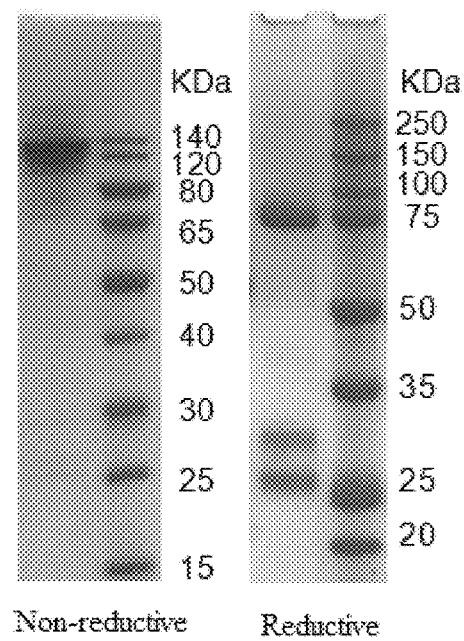
FIG. 3 shows an SDS-PAGE electrophoresis pattern of an anti-CD3/CD19 bispecific antibody protein.

The plasmids encoding three polypeptide chains of the bispecific antibodies, constructed as described above, were transformed into competent bacteria DH5α, respectively, and the bacteria were amplified by bacterial culture, from which the plasmid DNAs were purified. The purified plasmid DNAs were transiently transfected into 293F cells by co-transfection. A GFP plasmid was used as a positive control, and concurrently transfected into 293F cells for the observation of the transfection efficiency. The 293 cells were transfected with the plasmid having the anti-CD89/CD20 bispecific antibody and the plasmid having the anti-CD19/CD3 bispecific antibody, respectively, and after 48 hours of transfection, the expression amount of the recombinant antibodies was detected by ELISA double-antibody sandwich assay, demonstrating that both of the bispecific antibodies were well expressed. After 72 hours of transfection, the cultured supernatant of the transfected cells was collected, from which the antibody proteins were purified by Protein An affinity chromatography. The sample solution was filtered through a 0.45 μm filter before loading to remove impurities such as cells and polymers, and a ⅒ volume of a binding buffer was added thereto to allow the sample to have the same pH as the binding buffer. After the sample had flowed out, the column was rinsed with 5 mL (5~10 volumes) of the binding buffer. The purified bispecific antibodies were both analyzed by SDS-PAGE, which showed a 133 kD band in non-reductive electrophoresis, and 77 kD and 26~29 kD bands in reductive electrophoresis, being identical to the predicted molecular weight (FIG. 3).

Example 5

Figure 4:
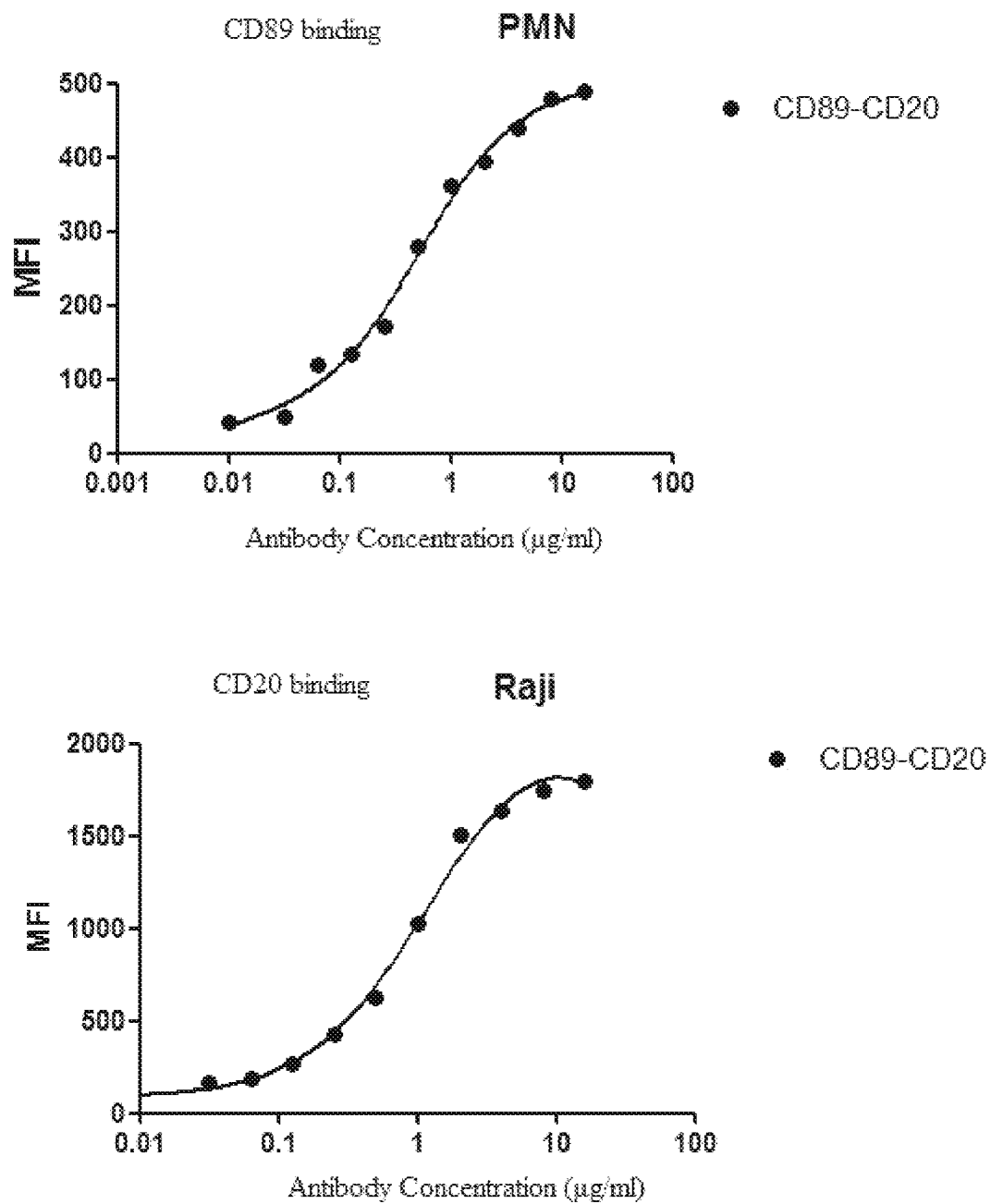
FIG. 4 shows the binding of an anti-CD89/CD20 bispecific antibody to PMN, Raji cells detected by flow cytometry.
Figure 5:
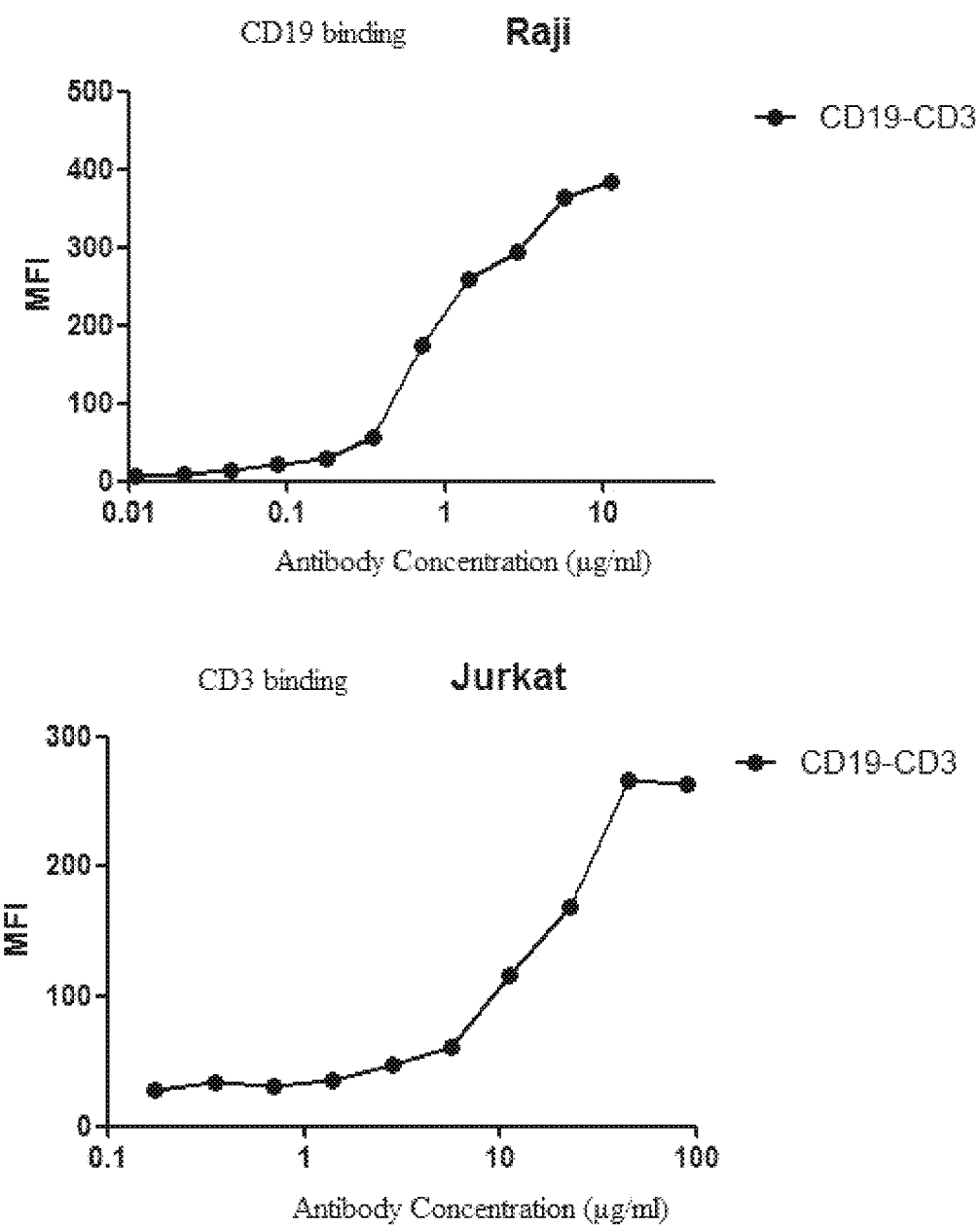
FIG. 5 shows the binding of an anti-CD19/CD3 bispecific antibody to Raji, Jurkat cells detected by flow cytometry.

Identification of Binding of Antibodies to Individual Targets by Flow Cytometer In order to identify the target binding ability of the anti-CD89/CD20 and anti-CD19/CD3 bispecific antibodies purified by protein A, CD19- and CD20-positive Raji cells (ATCC), CD89-positive PMN cells isolated from human peripheral blood, and CD3-positive Jurkat cells (ATCC) were subjected to a flow cytometric experiment. The three types of cells, Raji, PMN and Jurkat, were individually pipetted up and down into single cell suspensions. The cells were then resuspended in PBS followed by counting, from which $1×10^6$ cells were taken, added with the bispecific antibody with different dilutions, maintained in an ice bath for 45 minutes, and washed twice with PBS. Thereafter, a FITc-goat anti-human IgG (H+L) secondary antibody marker was added thereto, maintained in an ice bath for 45 minutes, and washed twice with PBS. The cells were resuspended in 500 μL of PBS and then added into a flow tube, which were detected by a flow cytometer to calculate the fluorescence intensity. A negative control group was a control with respect to an irrelevant antibody. The results showed that the two bispecific antibodies had a good affinity to their corresponding antigens (FIG. 4, FIG. 5).

Example 6

Figure 6:
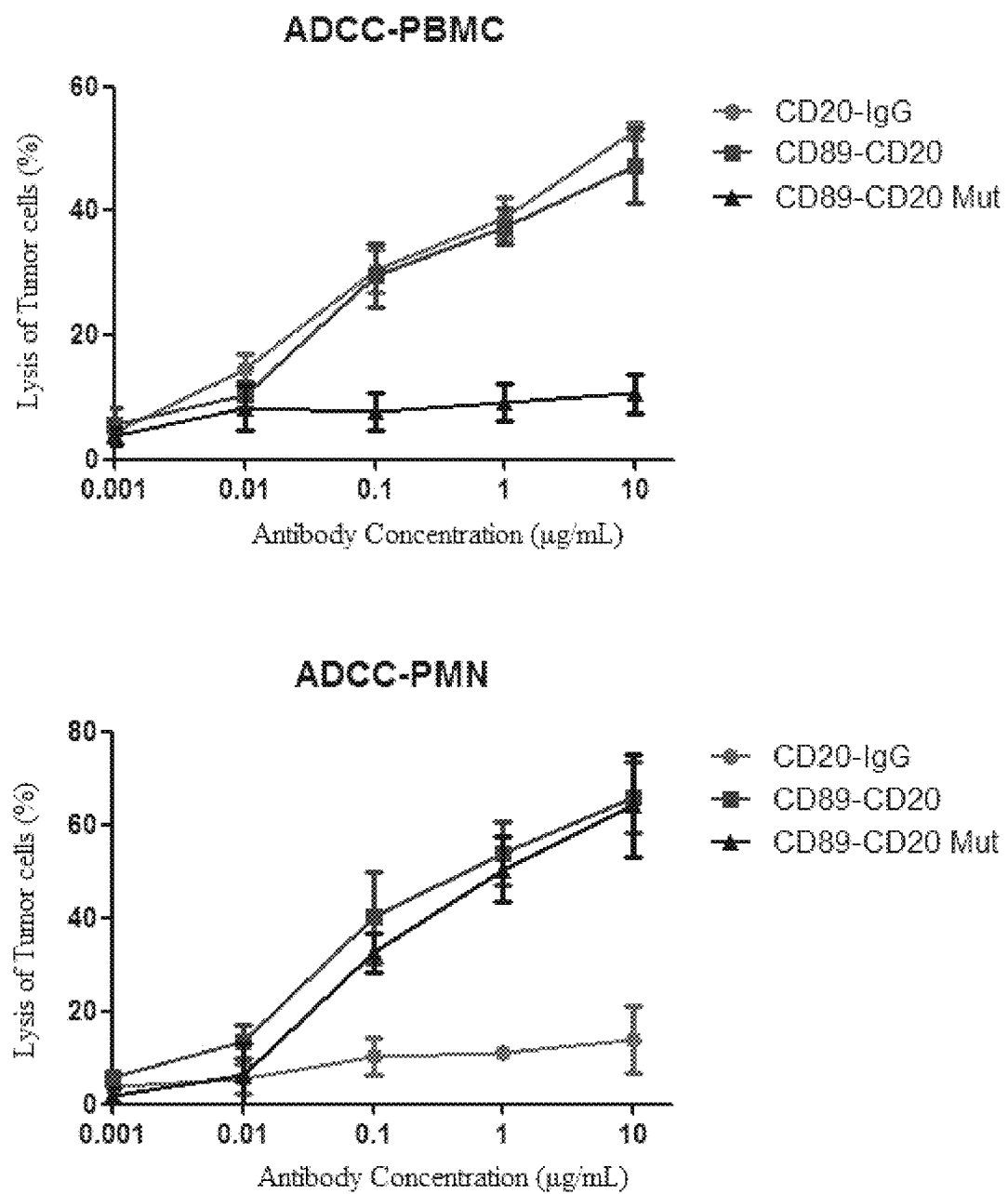
FIG. 6 shows the ability of an anti-CD89/CD20 bispecific antibody to kill tumor cells.

Detection of Killing Effect of Anti-CD89/CD20 Bispecific Antibody on Tumor Cells In order to determine the killing effect of the anti-CD89/CD20 bispecific antibody on CD20-positive cells, Raji cells were detected using a CytoTox 96 kit. The CytoTox 96 kit can be used to quantitatively detect the content of lactate dehydrogenase (LDH). LDH is a stable cytosolic enzyme and can be released when cells are lysed, of which the release type is substantially the same as that of [51Cr] in radioactive analysis, and the released amount is proportional to the number of the cells died. To a 96-well plate, a fixed number of Raji cells were added, and then effector cells that were human PMNs or PBMCs, the bispecific antibody diluted in different dilution gradients with 0.1% BSA/PBS (w/v), and a lysis solution (10×) were added thereto. After incubation for 4 hours, the culture was centrifuged at 250×g for 4 minutes. 50 μl of the supernatant was transferred from each well to a 96-well microplate using a pipette, respectively, and 50 μl of a substrate was added to each of the wells. The plate was covered with an aluminum foil or an opaque box to protect the plate from light, and incubated at room temperature for 30 minutes. The results are shown in FIG. 6.

In the presence of PMNs (mostly neutrophils), the anti-CD89/CD20 bispecific antibody could be very effective in killing the tumor cells, while the control group Rituximab antibody (CD20-Ig) could not kill the tumor cells by PMN mediation (PMN cells lacking NK cells). In addition, the anti-CD89/CD20 bispecific antibody killed the tumor cells independently of Fc-mediated ADCC, since the anti-CD89/CD20 bispecific antibody in which Fc was mutated (CD89-CD20 mut) to eliminate the ADCC function could still kill the tumor cells well (FIG. 6), indicating that the anti-CD89/CD20 bispecific antibody recruited PMN effector cells (mostly neutrophils) by CD89.

The anti-CD89/CD20 bispecific antibody of the present invention could kill the tumor cells in the presence of PBMCs, however, after the mutation of Fc (CD89-CD20 mut) to eliminate the ADCC function, this bispecific antibody lost its tumor killing ability, indicating that the killing ability through PBMCs was an Fc-mediated ADCC effect. Similarly, the control group Rituximab antibody (CD20-Ig) could effectively kill the tumor cells and act through ADCC.

The present inventors have successfully constructed a bispecific antibody for killing tumor cells by a cell killing function mediated by PMNs (mostly neutrophils) based on CD89 surface antigens for the first time. This is a breakthrough in the field of immunotherapy and opens up a new subdivided field.

Example 7

Figure 7:
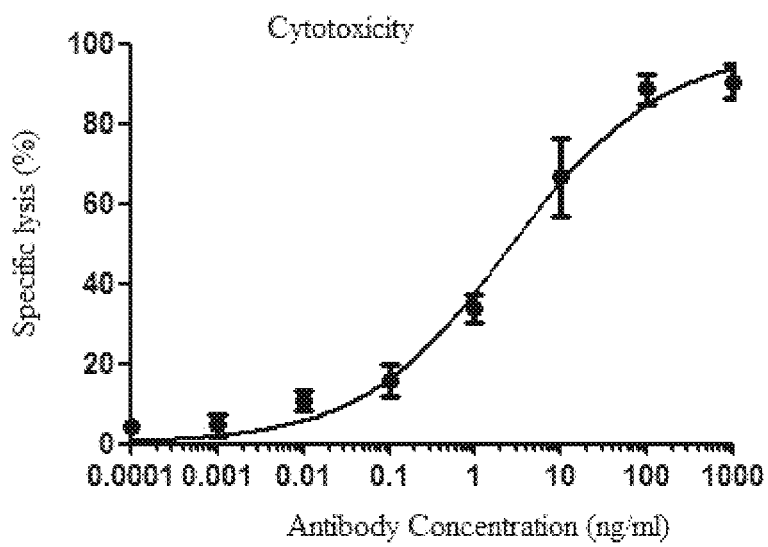
FIG. 7 shows the killing ability of T cells mediated by an anti-CD19/CD3 bispecific antibody in vitro.

Detection of In Vitro Killing Ability of Anti-CD19/CD3 Bispecific Antibody Mediated T Cells The killing effect of the anti-CD19/CD3 bispecific antibody on CD19-positive cells, that is the killing ability of T cells mediated by the antibody, was detected by using a CytoTox 96 non-radioactive cytotoxicity kit. The used T cells were derived from PBMC cells isolated from human fresh peripheral blood, and were activated by IL-2 (10 U/ml) and CD3 antibodies for 4~5 days and then collected for use. Tumor cells were Raji cells highly expressing CD19 antigens. The target/effector ratio of the tumor target cells to the effector T cells was 1:10. The working concentration of the bispecific antibody was obtained by a 10-fold gradient dilution. The results showed that the anti-CD19/CD3 bispecific antibody was very effective in mediating the killing effect of T cells on CD19-positive tumor cells, with an EC50 value of about 2 ng/mL (FIG. 7).

Such experiment results show that the asymmetric bispecific antibody of the present invention has a structure which cannot be used merely for the two specific targets CD89 and CD20, but can be used as a novel bispecific antibody platform which is widely applicable to a variety of different targets. Specifically, the structure of the asymmetric bispecific antibody of the present invention overcomes many defects in the prior art (e.g., BiTE technology), and the flexibility and adaptability of the spatial structure thereof allow the construction of many bispecific antibodies against different targets, which can be used in various applications.

Example 8

Detection of Serum Half-Life of Anti-CD89/CD20 Bispecific Antibody

Figure 8:
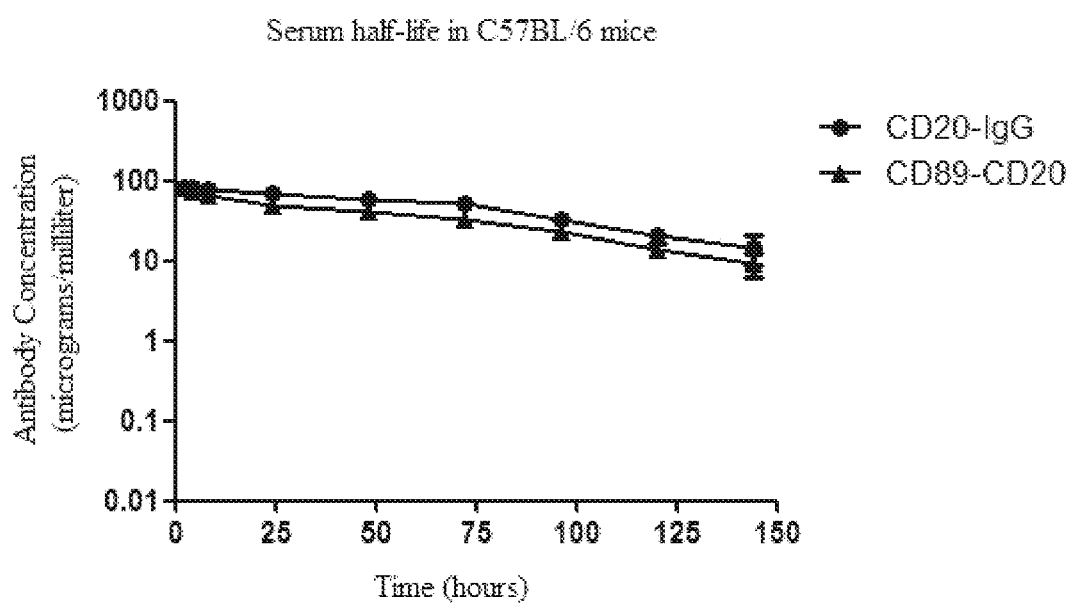
FIG. 8 shows the serum half-life of a bispecific antibody in mice.

The anti-CD89/CD20 bispecific antibody was used as an example to study its pharmacokinetics in animals. C57BL/6 female mice, aged 6~8 weeks, were divided into groups with 5 mice per group. Each of the mice was administered with Rituximab or the bispecific antibody by tail vein injection at 100 μg of the antibody per mouse. Blood was taken from the orbits at 2, 4, 8, 24, 48, 72, 96, 120, and 144 hours after the injection, and detected for the IgG content thereof by an ELISA double-antibody sandwich method (FIG. 8). As a result, it was surprisingly found that the bispecific antibody of the present invention had a longer half-life in vivo than BiTE (which has a half-life of only 2.1 hours), and had a similar half-life to that of Rituximab. Therefore, the antibody of the present invention combines both the advantages of the long half-life of common monoclonal antibodies and the bispecificity of existing bispecific antibodies, and provides a more powerful approach for the clinical treatment.

Example 9

In Vivo Therapeutic Experiment of Anti-CD89/CD20 Bispecific Antibody on Tumor

Figure 9:
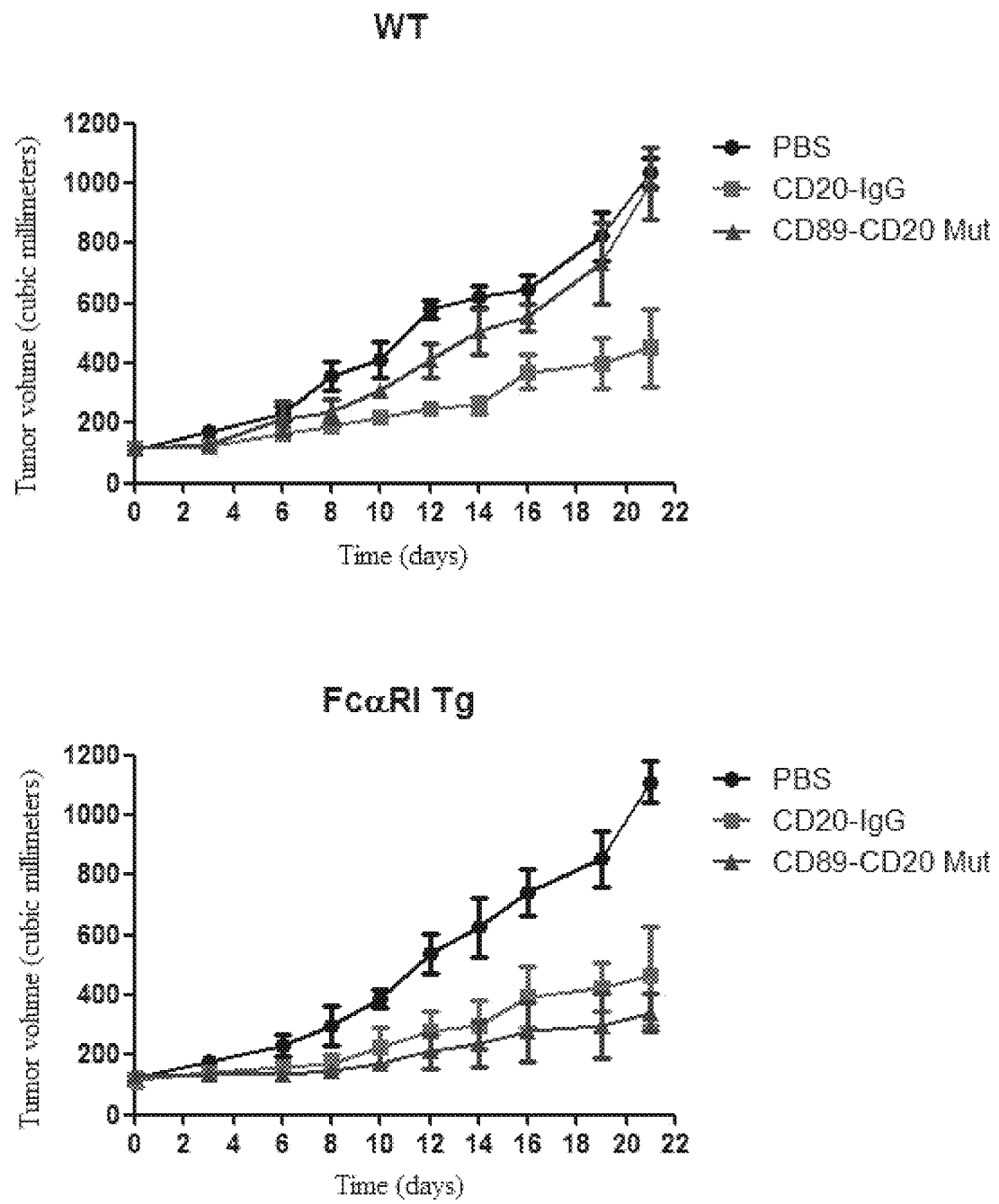
FIG. 9 shows in vivo therapeutic experiments for an anti-CD89/CD20 bispecific antibody against a tumor.

CD20-LLC cells (a mouse Lewis lung cancer cell line stably expressing human CD20 antigens) in the logarithmic growth phase were inoculated subcutaneously to the lateral side of the right hind limb of mice, in which each of the mice was inoculated with $1 \times 10^6$ cells. When the tumor volume was increased to about 100~150 mm$^3$ after inoculation, the mice were randomly divided into groups, with 6~8 mice per group, and each of the groups was administered by tail vein injection once a week. A treatment group was administered with a drug having a volume of 0.2 mL at a dose of 10 mg/kg, and a control group was administered PBS in the same volume. The length and width of the tumor in the mice were measured with a vernier caliper every three days, from which the tumor volume was calculated, and a tumor growth curve was plotted until the tumor in the PBS group grew to about 1000 mm$^3$. The results showed that in the wild-type mouse model test, the anti-CD89/CD20 bispecific antibody had a low tumor killing efficiency, which was substantially comparable to that in the PBS control group. This was because the wild mouse had no CD89 receptor and thus the anti-CD89/CD20 bispecific antibody substantially had no anti-tumor effect, and on the contrary, Rituximab had a good anti-tumor ability and can inhibit the tumor growth (FIG. 9). In order to determine the anti-tumor effect of the anti-CD89/CD20 bispecific antibody, studies were further performed in a FCαRI (CD89) transgenic mouse model. It was found that the anti-CD89/CD20 bispecific antibody had an ability to significantly inhibit the tumor growth, and unexpectedly, its anti-tumor effect was even significantly better than the commercialized Rituximab antibody (CD20-IgG) (FIG. 9).

Example 10

In Vivo Therapeutic Experiment of Anti-CD19/CD3 Bispecific Antibody on Tumor

Figure 10:
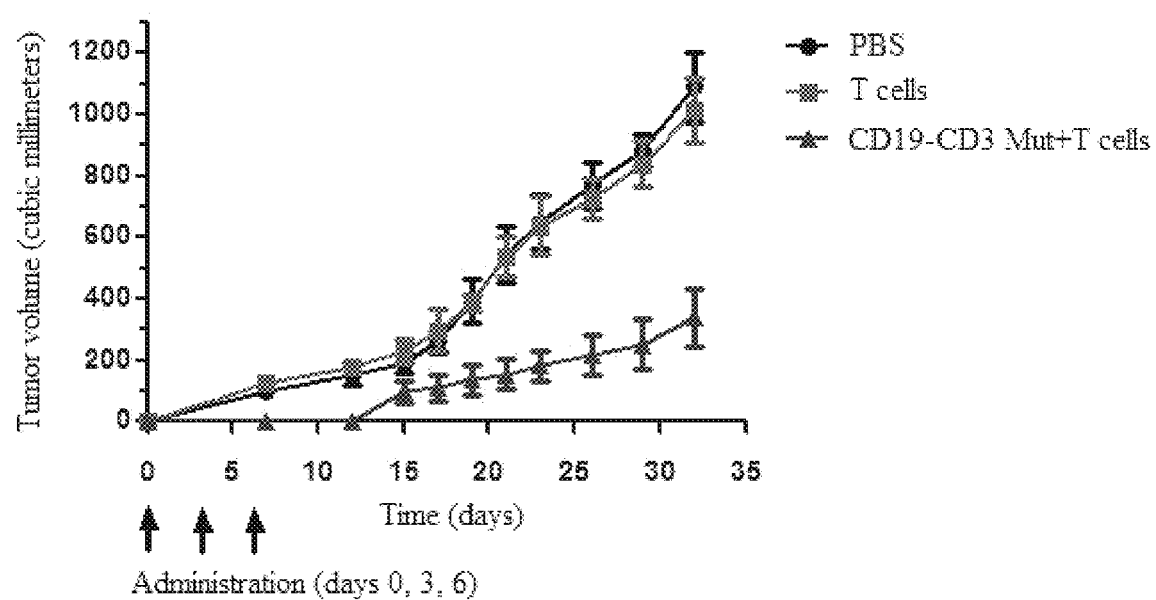
FIG. 10 shows in vivo therapeutic experiments for an anti-CD19/CD3 bispecific antibody against a tumor.

Raji cells in a logarithmic growth phase were inoculated subcutaneously to the lateral side of the right hind limb of nude mice, in which each of the mice was inoculated with a suspension having $3 \times 10^6$ cells, with 6~8 mice per group. At the same time, human T lymphocytes which had been previously amplified in vitro were injected into the mice by tail veins at a dose of $1 \times 10^7$ per mouse. Meanwhile, the anti-CD19/CD3 bispecific antibody was administered thereto by tail vein injection once every 3 days for total 3 times (days 0, 3, and 6), at a dose of 5 mg/kg. A PBS group was used as a control group, and a T cell group was only injected with T cells. The length and width of the tumor in the mice were measured with a vernier caliper about every three days, from which the tumor volume was calculated. A tumor growth curve was plotted from day 0, the day starting the administration for treatment, to the time at which the tumor in the PBS group grew to about 1000 mm$^3$. The results showed that, in the nude mouse-human T cell model test, the anti-CD19/CD3 bispecific antibody had a high tumor killing efficiency under an action of the activated T cells in vivo. The tumor reached a level of 100~150 mm$^3$ on day 15 after inoculation, which was significantly later than the PBS group. For mice which were injected only with T cells without treatment with the antibody drug, the tumor growth was substantially comparable to that in the PBS control group (FIG. 10).

The above description is only for preferred embodiments by way of example only and without limitation to the combination of features necessary for carrying the present invention into effect. The headings provided herein are not intended to limit the various embodiments of the present invention. Terms such as "including", "comprising" and "containing" are not intended to be limiting. In addition, unless otherwise indicated, the singular form "a", "an", or "the" includes plural references, as well as "or" means "and/or". Unless otherwise defined herein, all technical and scientific terms used herein have the same meaning as commonly understood by those skilled in the art.

All publications and patents mentioned in the present application are incorporated herein by reference. Without departing from the scope and spirit of the present invention, various modifications and variations of the described method and composition of the present invention will be apparent to those skilled in the art. Although the present invention has been described by using specific preferred embodiments, it should be understood that the claimed invention should not be unduly limited to these specific embodiments. In fact, many variations of the described modes for carrying out the invention that are obvious to those skilled in the art are intended to be included within the scope of the appended claims.

REFERENCES

[1] Sang J K, Youngwoo P, Hyo J H. Antibody engineering for the de velopment of therapeutic antibodies [J]. Mol Cell, 2005, 20: 17-29.
[2] Clynes R A, Towers T L, Presta L G, Ravetch J V. Inhibitory Fc receptors modulate in vivo cytoxicity against tumor targets. Nat Med 2000; 6:443-6.
[3] Stockmeyer B., M. Dechnat, M., et al. Triggering Fc alpha-recepter I(CD89) recruits neutrophils as effector cells of CD20-directed antibody therapy. J Imnunol. 165: 5954-5961.
[4] Kaxevanis C N, Papamichail M. Targeting of tumor cells by lympbocytes engineered to express chimeric receptor genes [J]. Cancer Immunol Immunother, 2004, 53(10): 893-903.
[5] Michael Dechant, Thomas Valerius. IgA antibodies for cancer therapy. [J] Critical Reviews in Oncology/Hematology, 39 (2001) 69-77.
[6] Van Egmond M, van Garderen E, van Spriel A B et al. Fc alpha RI positive liver Kupffer cells: reappraisal of the function of immunoglobulin A in immunity. [J]. Nat Med, 2000; 6 (6): 680.
[7] Phillip D Smith, Lesley E Smythies, Meg Mosteller Barnum et al. Intestinal macrophages lack CD14 and CD89 and consequently are downregulated for LPS and IgA mediated activities [J]. J of Immunology, 2001; 167: 2651.
[8] Honorio Franca A C, Launay P, Carneiro Sampaio M M et al. Colostral neutrophils express Fc alpha receptors (CD89) lacking gamma chain association and mediate noninflammatory properties of secretory IgA. [J]. Leukoc Biol, 2001; 69:289-293.
[9] Van Egmond M, van Garderen E, van Spriel A B et al. Fc alpha RI positive liver Kupffer cells: reappraisal of the function of immunoglobulin A in immunity. [J]. Nat Med, 2000; 6 (6):680.
[10] Fiederic Geissmann, Pierre Launay, Benoit Pasquire et al. A subset of human dendritic cells expresses IgA Fc receptor (CD89), which mediates internalization and activation upon crosslinking by IgA complexes. [J] J. of Immunology, 2001; 166:346-348.
[11] Herr A. B., C. L. Whiet, C. Miblunr, C. Wu, et al. Bivalent binding of IgAI to FcαRI suggests a mechanism for cytokine activation of IgA Phagoeytosis. [J]. J. Mol. Biol. 2003.327:645-657.
[12] Grosseetet, B., P. Luana, A. Lehuen, P. Jungers, J. E. Bach, and R. C. Monetior. Down-regulation of FcαRI on blood cells of IgA nephropathy patients: evidence for a negative regulatory role of seurm IgA. [J]. Kidney Int. 2003.53:1321-1335.
[13] Reterink, T. J., E. W. Levarht, N. K J et al. Transforming growth fator-beta 1 (TGF-beta 1) down-regulates IgA Fc-recepter (CD89) expression on human monocytes. [J]. Clin. Exp Immunol. 1996.103:161-166.
[14] Sehiell, rC., A. SPittle, M. Willheim et al. Influence of suramim on the experssion of Fc receptor on human monocytes and U937cells, and on their phagocytic properties. [J]. Immunology 1994.81:598-604.
[15] Solinas G, Germano G, Mantovani A, Allavena P. Tumor-associated macrophages (TAM) as major players of the cancer-related inflammation. [J]. J Leukoc Biol. 2009, 86(5):1065-73.
[16] Sica A, Schioppa T, Mantovani A, Allavena P. Tumour-associated macrophages are a distinct M2 polarised population promoting tumour progression: potential targets of anti-cancer therapy. [J]. Eur J Cancer. 2006, 42(6):717-27.
[17] Bakema J E, Ganzevles S H, Fluitsma D M, etc. Targeting FcαRI on polymorphonuclear cells induces tumor cell killing through autophagy. [J]. Immunol. 2011, 187(2):726-32.
[18] Ridgway, et al., 'Knobs-into-holes' engineering of antibody CH3 domains for heavy chain heterodimerization. Protein Engineering vol. 9 no. 7 pp. 617-621, 1996

```
Amino acid sequence of the first chain (antibody VL and CL of
anti-CD89 light chain)
                                                          SEQ ID NO: 1
AspIleGlnMetThrGlnSerProSerSerLeuSerAlaSerLeuGlyGluArgValSer LeuThrCysArgAlaSerGlnAspIleGlySerSerLeuAsnTrpLeuGlnGlnGluPro AspGlyThrIleLysArgLeuIleTyrAlaThrSerSerLeuAspSerGlyValProGlu
```

-continued

ArgPheSerGlySerArgSerGlySerHisTyrSerLeuThrIleSerSerLeuGluSer

GluAspPheValAspTyrTyrCysLeuGlnTyrAlaSerTyrProTrpThrPheGlyGly

GlyThrLysLeuGluIleLysArgThrValAlaAlaProSerValPheIlePheProPro

SerAspGluGlnLeuLysSerGlyThrAlaSerValValCysLeuLeuAsnAsnPheTyr

ProArgGluAlaLysValGlnTrpLysValAspAsnAlaLeuGlnSerGlyAsnSerGln

GluSerValThrGluGlnAspSerLysAspSerThrTyrSerLeuSerSerThrLeuThr

LeuSerLysAlaAspTyrGluLysHisLysValTyrAlaCysGluValThrHisGlnGly

LeuSerSerProValThrLysSerPheAsnArgGlyGluCys

Amino acid sequence of antibody VH and CH1 of anti-CD89 heavy chain in the second chain

SEQ ID NO: 2

GlnIleGlnLeuValGlnSerGlyProGluLeuLysLysProGlyGluThrValLysIle

SerCysLysAlaSerGlyTyrValPheThrAsnTyrGlyMetAsnTrpValLysGlnThr

ProGlyLysGlyLeuLysTrpMetGlyTrpIleAsnThrTyrThrGlyArgProThrSer

AlaAspAspPheLysGlyArgPheAlaPheSerLeuGluThrSerAlaSerThrAlaTyr

LeuGlnIleAsnAsnLeuLysAsnGluAspThrAlaThrTyrPheCysSerSerGlnGly

PheSerPheThrSerTrpGlyGlnGlyThrLeuValThrValSerAlaAlaSerThrLys

GlyProSerValPheProLeuAlaProSerSerLysSerThrSerGlyGlyThrAlaAla

LeuGlyCysLeuValLysAspTyrPheProGluProValThrValSerTrpAsnSerGly

AlaLeuThrSerGlyValHisThrPheProAlaValLeuGlnSerSerGlyLeuTyrSer

LeuSerSerValValThrValProSerSerSerLeuGlyThrGlnThrTyrIleCysAsn

ValAsnHisLysProSerAsnThrLysValAspLysLysValGluProLysSerCys

Amino acid sequence of scFv region of the second chain (ScFv of anti-CD20)

SEQ ID NO: 3

GlnAlaTyrLeuGlnGlnSerGlyAlaGluLeuValArgProGlyAlaSerValLysMet

SerCysLysAlaSerGlyTyrThrPheThrSerTyrAsnMetHisTrpValLysGlnThr

ProArgGlnGlyLeuGluTrpIleGlyAlaIleTyrProGlyAsnGlyAspThrSerTyr

AsnGlnLysPheLysGlyLysAlaThrLeuThrValAspLysSerSerSerThrAlaTyr

MetGlnLeuSerSerLeuThrSerGluAspSerAlaValTyrPheCysAlaArgValVal

TyrTyrSerAsnSerTyrTrpTyrPheAspValTrpGlyThrGlyThrThrValThrVal

SerGlyGlyGlyGlySerGlyGlyGlyGlySerGlyGlyGlyGlySerGlnIleValLeu

SerGlnSerProAlaIleLeuSerAlaSerProGlyGluLysValThrMetThrCysArg

AlaSerSerSerValSerTyrMetHisTrpTyrGlnGlnLysProGlySerSerProLys

ProTrpIleTyrAlaProSerAsnLeuAlaSerGlyValProAlaArgPheSerGlySer

GlySerGlyThrSerTyrSerLeuThrIleSerArgValGluAlaGluAspAlaAlaThr

TyrTyrCysGlnGlnTrpSerPheAsnProProThrPheGlyAlaGlyThrLysLeuGlu

Leu

Amino acid sequence of Fc region of the second chain (Fc-Hole fragment)

SEQ ID NO: 4

AspLysThrHisThrCysProProCysProAlaProGluLeuLeuGlyGlyProSerVal

PheLeuPheProProLysProLysAspThrLeuMetIleSerArgThrProGluValThr

CysValValValAspValSerHisGluAspProGluValLysPheAsnTrpTyrValAsp

GlyValGluValHisAsnAlaLysThrLysProArgGluGluGlnTyrAlaSerThrTyr

ArgValValSerValLeuThrValLeuHisGlnAspTrpLeuAsnGlyLysGluTyrLys

CysLysValSerAsnLysAlaLeuProAlaProIleGluLysThrIleSerLysAlaLys

GlyGlnProArgGluProGlnValTyrThrLeuProProSerArgAspGluLeuThrLys

AsnGlnValSerLeuSerCysAlaValLysGlyPheTyrProSerAspIleAlaValGlu

TrpGluSerAsnGlyGlnProGluAsnAsnTyrLysThrThrProProValLeuAspSer

AspGlySerPhePheLeuValSerLysLeuThrValAspLysSerArgTrpGlnGlnGly

AsnValPheSerCysSerValMetHisGluAlaLeuHisAsnHisTyrThrGlnLysSer

LeuSerLeuSerProGlyLys

Amino acid sequence of Fc region of the third chain (Fc-Knob fragment)

SEQ ID NO: 5

AspLysThrHisThrCysProProCysProAlaProGluLeuLeuGlyGlyProSerVal

PheLeuPheProProLysProLysAspThrLeuMetIleSerArgThrProGluValThr

CysValValValAspValSerHisGluAspProGluValLysPheAsnTrpTyrValAsp

GlyValGluValHisAsnAlaLysThrLysProArgGluGluGlnTyrAlaSerThrTyr

ArgValValSerValLeuThrValLeuHisGlnAspTrpLeuAsnGlyLysGluTyrLys

CysLysValSerAsnLysAlaLeuProAlaProIleGluLysThrIleSerLysAlaLys

GlyGlnProArgGluProGlnValTyrThrLeuProProSerArgAspGluLeuThrLys

AsnGlnValSerLeuTrpCysLeuValLysGlyPheTyrProSerAspIleAlaValGlu

TrpGluSerAsnGlyGlnProGluAsnAsnTyrLysThrThrProProValLeuAspSer

AspGlySerPhePheLeuTyrSerLysLeuThrValAspLysSerArgTrpGlnGlnGly

AsnValPheSerCysSerValMetHisGluAlaLeuHisAsnHisTyrThrGlnLysSer

LeuSerLeuSerProGlyLys

Amino acid sequence of the sequence of the first chain (antibody VL and CL of anti-CD19 light chain)

SEQ ID NO: 6

AspIleGlnLeuThrGlnSerProAlaSerLeuAlaValSerLeuGlyGlnArgAlaThr

IleSerCysLysAlaSerGlnSerValAspTyrAspGlyAspSerTyrLeuAsnTrpTyr

GlnGlnIleProGlyGlnProProLysLeuLeuIleTyrAspAlaSerAsnLeuValSer

GlyIleProProArgPheSerGlySerGlySerGlyThrAspPheThrLeuAsnIleHis

ProValGluLysValAspAlaAlaThrTyrHisCysGlnGlnSerThrGluAspProTrp

ThrPheGlyGlyGlyThrLysLeuGluIleLysArgThrValAlaAlaProSerValPhe

IlePheProProSerAspGluGlnLeuLysSerGlyThrAlaSerValValCysLeuLeu

AsnAsnPheTyrProArgGluAlaLysValGlnTrpLysValAspAsnAlaLeuGlnSer

GlyAsnSerGlnGluSerValThrGluGlnAspSerLysAspSerThrTyrSerLeuSer

SerThrLeuThrLeuSerLysAlaAspTyrGluLysHisLysValTyrAlaCysGluVal

ThrHisGlnGlyLeuSerSerProValThrLysSerPheAsnArgGlyGluCys

Amino acid sequence of antibody VH and CH1 of anti-CD19 heavy chain in the second chain

SEQ ID NO: 7

GlnValGlnLeuGlnGlnSerGlyAlaGluLeuValArgProGlySerSerValLysIle

SerCysLysAlaSerGlyTyrAlaPheSerSerTyrTrpMetAsnTrpValLysGlnArg

ProGlyGlnGlyLeuGluTrpIleGlyGlnIleTrpProGlyAspGlyAspThrAsnTyr

AsnGlyLysPheLysGlyLysAlaThrLeuThrAlaAspGluSerSerSerThrAlaTyr

MetGlnLeuSerSerLeuAlaSerGluAspSerAlaValTyrPheCysAlaArgArgGlu

ThrThrThrValGlyArgTyrTyrTyrAlaMetAspTyrTrpGlyGlnGlyThrThrVal

-continued

ThrValSerSerAlaSerThrLysGlyProSerValPheProLeuAlaProSerSerLys

SerThrSerGlyGlyThrAlaAlaLeuGlyCysLeuValLysAspTyrPheProGluPro

ValThrValSerTrpAsnSerGlyAlaLeuThrSerGlyValHisThrPheProAlaVal

LeuGlnSerSerGlyLeuTyrSerLeuSerSerValValThrValProSerSerSerLeu

GlyThrGlnThrTyrIleCysAsnValAsnHisLysProSerAsnThrLysValAspLys

LysValGluProLysSerCys

| Amino acid sequence of scFv region of the second chain (ScFv of anti-CD3) | SEQ ID NO: 8 |
|---|---|

AspIleLysLeuGlnGlnSerGlyAlaGluLeuAlaArgProGlyAlaSerValLysMet

SerCysLysThrSerGlyTyrThrPheThrArgTyrThrMetHisTrpValLysGlnArg

ProGlyGlnGlyLeuGluTrpIleGlyTyrIleAsnProSerArgGlyTyrThrAsnTyr

AsnGlnLysPheLysAspLysAlaThrLeuThrThrAspLysSerSerSerThrAlaTyr

MetGlnLeuSerSerLeuThrSerGluAspSerAlaValTyrTyrCysAlaArgTyrTyr

AspAspHisTyrCysLeuAspTyrTrpGlyGlnGlyThrThrLeuThrValSerSerVal

GluGlyGlySerGlyGlySerGlyGlySerGlyGlyValAspAspIleGln

LeuThrGlnSerProAlaIleMetSerAlaSerProGlyGluLysValThrMetThrCys

ArgAlaSerSerSerValSerTyrMetAsnTrpTyrGlnGlnLysSerGlyThrSerPro

LysArgTrpIleTyrAspThrSerLysValAlaSerGlyValProTyrArgPheSerGly

SerGlySerGlyThrSerTyrSerLeuThrIleSerSerMetGluAlaGluAspAlaAla

ThrTyrTyrCysGlnGlnTrpSerSerAsnProLeuThrPheGlyAlaGlyThrLysLeu

GluLeuLys

| VL of anti-CD89 antibody CDR1 | SEQ ID NO: 9 |
|---|---|
| GlnAspIleGlySerSer | |

| VL of anti-CD89 antibody CDR2 | SEQ ID NO: 10 |
|---|---|
| AlaThrSer | |

| VL of anti-CD89 antibody CDR3 | SEQ ID NO: 11 |
|---|---|
| LeuGlnTyrAlaSerTyrProTrpThr | |

| VH of anti-CD89 antibody CDR1 | SEQ ID NO: 12 |
|---|---|
| GlyTyrValPheThrAsnTyrGly | |

| VH of anti-CD89 antibody CDR2 | SEQ ID NO: 13 |
|---|---|
| IleAsnThrTyrThrGlyArgPro | |

| VH of anti-CD89 antibody CDR3 | SEQ ID NO: 14 |
|---|---|
| SerSerGlnGlyPheSerPheThrSer | |

| VL of anti-CD19 antibody CDR1 | SEQ ID NO: 15 |
|---|---|
| GlnSerValAspTyrAspGlyAspSerTyr | |

| VL of anti-CD19 antibody CDR2 | SEQ ID NO: 16 |
|---|---|
| AspAlaSer | |

| VL of anti-CD19 antibody CDR3 | SEQ ID NO: 17 |
|---|---|
| GlnGlnSerThrGluAspProTrpThr | |

| VH of anti-CD19 antibody CDR1 | SEQ ID NO: 18 |
|---|---|
| GlyTyrAlaPheSerSerTyrTrp | |

VH of anti-CD19 antibody CDR2

SEQ ID NO: 19

IleTrpProGlyAspGlyAspThr

VH of anti-CD19 antibody CDR3

SEQ ID NO: 20

AlaArgArgGluThrThrThrValGlyArgTyrTyrTyrAlaMetAspTyr

DNA sequence of variable region of anti-CD89 heavy chain

SEQ ID NO: 21

```
  1    ATGGTCAGCT ACTGGGACAC CGGGGTCCTG CTGTGCGCGC TGCTCAGCTG TCTGCTTCTC
 61    ACAGGATCTA GTTCCGGACA GATCCAGTTG GTGCAATCTG GACCTGAGCT GAAGAAGCCC
121    GGAGAGACAG TCAAGATCTC CTGCAAGGCT TCGGGGTATG TCTTCACAAA CTATGGAATG
181    AACTGGGTGA AGCAGACTCC AGGAAAGGGT TTAAAGTGGA TGGGCTGGAT AAACACCTAC
241    ACTGGCAGGC CAACATCTGC TGATGACTTC AAGGGACGGT TTGCCTTCTC TTTGGAAACC
301    TCTGCCAGCA CTGCCTATTT GCAGATCAAC AACCTCAAAA ATGAGGACAC GGCTACATAT
361    TTCTGTTCAA GCCAGGGGTT TTCGTTTACT TCCTGGGGCC AGGGGACTCT GGTCACTGTC
421    TCTGCA
```

DNA sequence of variable region of anti-CD89 light chain

SEQ ID NO: 22

```
  1    ATGGTCAGCT ACTGGGACAC CGGGGTCCTG CTGTGCGCGC TGCTCAGCTG TCTGCTTCTC
 61    ACAGGATCTA GTTCCGGAGA CATCCAGATG ACCCAGTCTC CATCCTCCTT ATCTGCCTCT
121    CTGGGAGAAA GAGTCAGTCT CACTTGTCGG GCAAGTCAGG ACATTGGTAG TAGTTTAAAC
181    TGGCTTCAGC AGGAACCAGA TGGAACTATT AAACGCCTGA TCTACGCCAC ATCCAGTTTA
241    GATTCTGGTG TCCCCGAAAG GTTCAGTGGC AGTAGGTCTG GGTCACATTA TTCTCTCACC
301    ATCAGCAGCC TTGAGTCTGA AGATTTTGTA GACTATTACT GTCTACAATA TGCTAGTTAT
361    CCGTGGACGT TCGGTGGAGG CACCAAGCTG GAAATCAAA
```

Amino acid sequence of variable region of anti-CD89 heavy chain

SEQ ID NO: 23

GlnIleGlnLeuValGlnSerGlyProGluLeuLysLysProGlyGluThrValLysIleSerCysLysAlaSerGly

TyrValPheThrAsnTyrGlyMetAsnTrpValLysGlnThrProGlyLysGlyLeuLysTrpMetGlyTrpIleAsn

ThrTyrThrGlyArgProThrSerAlaAspAspPheLysGlyArgPheAlaPheSerLeuGluThrSerAlaSerThr

AlaTyrLeuGlnIleAsnAsnLeuLysAsnGluAspThrAlaThrTyrPheCysSerSerGlnGlyPheSerPheThr

SerTrpGlyGlnGlyThrLeuValThrValSerAla

Amino acid sequence of variable region of anti-CD89 light chain

SEQ ID NO: 24

AspIleGlnMetThrGlnSerProSerSerLeuSerAlaSerLeuGlyGluArgValSerLeuThrCysArgAlaSer

GlnAspIleGlySerSerLeuAsnTrpLeuGlnGlnGluProAspGlyThrIleLysArgLeuIleTyrAlaThrSer

SerLeuAspSerGlyValProGluArgPheSerGlySerArgSerGlySerHisTyrSerLeuThrIleSerSerLeu

GluSerGluAspPheValAspTyrTyrCysLeuGlnTyrAlaSerTyrProTrpThrPheGlyGlyGlyThrLysLeu

GluIleLys

Upstream primer of anti-CD89 VL fragment

SEQ ID NO: 25

TAAGCTTGGTACCGAGCTCGGATCCGCCGCCACCATGGTCAGCTACTGGGACACC

Downstream primer of anti-CD89 VL fragment

SEQ ID NO: 26

GATGGTGCAGCCACAGTTCGTTTGATTTCCAGCTTGGTGC

Upstream primer of CL fragment

SEQ ID NO: 27

GCACCAAGCTGGAAATCAAACGAACTGTGGCTGCACCATC

Downstream primer of CL fragment

SEQ ID NO: 28

GCGGGCCCTCTAGACTCGAGCGGCCGCGTCGACCTAACACTCTCCCCTGTTGAAGCTCT

-continued

| | |
|---|---|
| Upstream primer of CD89 VH fragment<br>TAAGCTTGGTACCGAGCTCGGATCCGCCGCCACCATGGTCAGCTACTGGGACACC | SEQ ID NO: 29 |
| Downstream primer of CD89 VH fragment<br>GATGGGCCCTTGGTGGAGGCTGCAGAGACAGTGACCAGAG | SEQ ID NO: 30 |
| Upstream primer of human IgG constant region<br>CTCTGGTCACTGTCTCTGCAGCCTCCACCAAGGGCCCATC | SEQ ID NO: 31 |
| Downstream primer of human IgG constant region<br>TTTACCCGGAGACAGGGAGAGGCTCTTCTGCGTG | SEQ ID NO: 32 |
| Upstream primer of CD20 ScFv fragment<br>GTGGTGGTAGCGGTGGCGGTGGTAGTCAGGCTTATTTGCAACAGTCTGGCGCG | SEQ ID NO: 33 |
| Downstream primer of CD20 ScFv fragment<br>CCAAGCTGGAGCTGGAATAGGTCGACGCGGCCGCTCGAGTCTAGAGGGCCCGCG | SEQ ID NO: 34 |
| Upstream primer of human Fc (knob) containing hinge region<br>AAGCTTGGTACCGAGCTCGGATCCGCCGCCACCATGGTCAGCTACTGGGACAC | SEQ ID NO: 35 |
| Downstream primer of human Fc (knob) containing hinge region<br>CGCGGGCCCTCTAGACTCGAGCGGCCGCGTCGACCTATTTACCCGGAGACAGGGAGAG | SEQ ID NO: 36 |
| Amino acid sequence of variable region of anti-CD19 light chain<br>AspIleGlnLeuThrGlnSerProAlaSerLeuAlaValSerLeuGlyGlnArgAlaThr<br>IleSerCysLysAlaSerGlnSerValAspTyrAspGlyAspSerTyrLeuAsnTrpTyr<br>GlnGlnIleProGlyGlnProProLysLeuLeuIleTyrAspAlaSerAsnLeuValSer<br>GlyIleProProArgPheSerGlySerGlySerGlyThrAspPheThrLeuAsnIleHis<br>ProValGluLysValAspAlaAlaThrTyrHisCysGlnGlnSerThrGluAspProTrp<br>ThrPheGlyGlyGlyThrLysLeuGluIleLys | SEQ ID NO: 37 |
| Amino acid sequence of variable region of anti-CD19 heavy chain<br>GlnValGlnLeuGlnGlnSerGlyAlaGluLeuValArgProGlySerSerValLysIle<br>SerCysLysAlaSerGlyTyrAlaPheSerSerTyrTrpMetAsnTrpValLysGlnArg<br>ProGlyGlnGlyLeuGluTrpIleGlyGlnIleTrpProGlyAspGlyAspThrAsnTyr<br>AsnGlyLysPheLysGlyLysAlaThrLeuThrAlaAspGluSerSerSerThrAlaTyr<br>MetGlnLeuSerSerLeuAlaSerGluAspSerAlaValTyrPheCysAlaArgArgGlu<br>ThrThrThrValGlyArgTyrTyrTyrAlaMetAspTyrTrpGlyGlnGlyThrThrVal<br>ThrValSerSer | SEQ ID NO: 38 |
| Upstream primer of anti-CD19 VL fragment<br>GTCTGCTTCTCACAGGATCTAGTTCCGGAGATATCCAACTGACCCAGAGC | SEQ ID NO: 39 |
| Downstream primer of anti-CD19 VL fragment<br>GATGGTGCAGCCACAGTTCGCTTGATTTCCAGTTTTGTGC | SEQ ID NO: 40 |
| Upstream primer of CL fragment<br>AAACTGGAAATCAAGCGAACTGTGGCTGCACCATCTGTCTTC | SEQ ID NO: 41 |
| Downstream primer of CL fragment<br>GCGGGCCCTCTAGACTCGAGCGGCCGCGTCGACCTAACACTCTCCCCTGTTGAAGCTCT | SEQ ID NO: 42 |
| Upstream primer of anti-CD19 VH fragment<br> | SEQ ID NO: 43 |

TCTGCTTCTCACAGGATCTAGTTCCGGACAGGTGCAGCTCCAGCAAAGC

Downstream primer of anti-CD19 VH fragment

SEQ ID NO: 44

GATGGGCCCTTGGTGGAGGCGCTGCTCACTGTCACTGTGG

Upstream primer of human IgG constant region fragment

SEQ ID NO: 45

GGGAACCACAGTGACAGTGAGCAGCGCCTCCACCAAGGGCCCATCGGT

Downstream primer of human IgG constant region fragment

SEQ ID NO: 46

TTTACCCGGAGACAGGGAGAGGCTCTTCTGCGTG

Upstream primer of anti-CD3 ScFv fragment

SEQ ID NO: 47

GGTAGTGACATCAAACTCCAACAGAGCGGAGCCGAAC

Downstream primer of anti-CD3 ScFv fragment

SEQ ID NO: 48

GCGGGCCCTCTAGACTCGAGCGGCCGCGTCGACCTACTTCAGCTCCAGCTTGGTGCCG

Sequence of Fc region of the second chain containing no mutation from Asn at position 297 to Ala in Fc region (Fc-hole fragment)

SEQ ID NO: 49

AspLysThrHisThrCysProProCysProAlaProGluLeuLeuGlyGlyProSerVal

PheLeuPheProProLysProLysAspThrLeuMetIleSerArgThrProGluValThr

CysValValValAspValSerHisGluAspProGluValLysPheAsnTrpTyrValAsp

GlyValGluValHisAsnAlaLysThrLysProArgGluGluGlnTyrAsnSerThrTyr

ArgValValSerValLeuThrValLeuHisGlnAspTrpLeuAsnGlyLysGluTyrLys

CysLysValSerAsnLysAlaLeuProAlaProIleGluLysThrIleSerLysAlaLys

GlyGlnProArgGluProGlnValTyrThrLeuProProSerArgAspGluLeuThrLys

AsnGlnValSerLeuSerCysAlaValLysGlyPheTyrProSerAspIleAlaValGlu

TrpGluSerAsnGlyGlnProGluAsnAsnTyrLysThrThrProProValLeuAspSer

AspGlySerPhePheLeuValSerLysLeuThrValAspLysSerArgTrpGlnGlnGly

AsnValPheSerCysSerValMetHisGluAlaLeuHisAsnHisTyrThrGlnLysSer

LeuSerLeuSerProGlyLys

Sequence of Fc region of the third chain containing no mutation from Asn at position 297 to Ala in Fc region (Fc-knob fragment)

SEQ ID NO: 50

AspLysThrHisThrCysProProCysProAlaProGluLeuLeuGlyGlyProSerVal

PheLeuPheProProLysProLysAspThrLeuMetIleSerArgThrProGluValThr

CysValValValAspValSerHisGluAspProGluValLysPheAsnTrpTyrValAsp

GlyValGluValHisAsnAlaLysThrLysProArgGluGluGlnTyrAsnSerThrTyr

ArgValValSerValLeuThrValLeuHisGlnAspTrpLeuAsnGlyLysGluTyrLys

CysLysValSerAsnLysAlaLeuProAlaProIleGluLysThrIleSerLysAlaLys

GlyGlnProArgGluProGlnValTyrThrLeuProProSerArgAspGluLeuThrLys

AsnGlnValSerLeuTrpCysLeuValLysGlyPheTyrProSerAspIleAlaValGlu

TrpGluSerAsnGlyGlnProGluAsnAsnTyrLysThrThrProProValLeuAspSer

AspGlySerPhePheLeuTyrSerLysLeuThrValAspLysSerArgTrpGlnGlnGly

AsnValPheSerCysSerValMetHisGluAlaLeuHisAsnHisTyrThrGlnLysSer

LeuSerLeuSerProGlyLys

DNA sequence of IgG constant region (containing Fc-hole fragment) by artificial gene synthesis

SEQ ID NO: 51

GCCTCCACCAAGGGCCCATCGGTCTTCCCCCTGGCACCCTCCTCCAAGAGCACCTC

-continued
```
TGGGGGCACAGCAGCCCTGGGCTGCCTGGTCAAGGACTACTTCCCCGAACCGGTG

ACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGC

AGCTTGGGCACCCAGACCTACATCTGCAACGTGAATCACAAGCCCAGCAACACCA

AGGTGGACAAGAAAGTTGAGCCCAAATCTTGTGACAAAACTCACACATGCCCACC

GTGCCCAGCACCTGAACTCCTGGGGGGACCGTCAGTCTTCCTCTTCCCCCCAAAA

CCCAAGGACACCCTCATGATCTCCCGGACCCCTGAGGTCACATGCGTGGTGGTGG

ACGTGAGCCACGAAGACCCTGAGGTCAAGTTCAACTGGTACGTGGACGGCGTGG

AGGTGCATAATGCCAAGACAAAGCCGCGGGAGGAGCAGTACAACAGCACGTACC

GTGTGGTCAGCGTCCTCACCGTCCTGCACCAGGACTGGCTGAATGGCAAGGAGTA

CAAGTGCAAGGTCTCCAACAAAGCCCTCCCAGCCCCCATCGAGAAAACCATCTCC

AAAGCCAAAGGGCAGCCCCGAGAACCACAGGTGTACACCCTGCCCCCATCCCGG

GATGAGCTGACCAAGAACCAGGTCAGCCTGTCCTGCGCGGTCAAAGGCTTCTATC

CCAGCGACATCGCCGTGGAGTGGGAGAGCAATGGGCAGCCGGAGAACAACTACA

AGACCACGCCTCCCGTGCTGGACTCCGACGGCTCCTTCTTCCTCGTCAGCAAGCTC

ACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGTAA

A
```
DNA sequence of anti-CD20-scFv by artificial gene synthesis
SEQ ID NO: 52
```
  1    CAGGCTTATT TGCAACAGTC TGGCGCGGAA CTTGTAAGAC CAGGGGCTTC TGTGAAGATG

61    AGCTGCAAGG CTAGTGGATA TACATTCACG TCCTATAATA TGCACTGGGT CAAGCAGACT

121    CCCCGGCAAG GCCTGGAATG GATCGGAGCA ATCTACCCTG GTAACGGAGA TACCTCCTAT

181    AATCAGAAAT TCAAGGGGAA AGCCACCCTT ACCGTGGATA ATCTAGTAG CACCGCCTAC

241    ATGCAGCTGT CCTCACTCAC ATCAGAGGAC TCCGCCGTCT ACTTCTGTGC CCGCGTGGTT

301    TACTATTCAA ACAGCTACTG GTACTTTGAC GTTTGGGGA CAGGCACCAC TGTGACTGTG

361    AGCGGTGGTG GTGGTTCTGG CGGCGGCGGC TCCGGTGGTG GTGGTTCTCA AATTGTGCTG

421    TCCCAGTCCC CGGCCATCCT TTCAGCCAGT CCAGGAGAAA AGTCACGAT GACCTGTAGA

481    GCTTCCTCAA GTGTGTCTTA TATGCACTGG TATCAGCAGA AGCCAGGATC ATCTCCCAAA

541    CCATGGATAT ACGCCCCTTC CAATCTCGCC AGCGGAGTCC CTGCACGCTT CAGCGGTAGC

601    GGCTCTGGGA CTTCTTACAG TCTCACTATC AGTAGGGTGG AAGCTGAGGA CGCAGCCACA

661    TACTATTGCC AGCAATGGAG CTTTAACCCC CCACATTCG GCGCTGGCAC CAAGCTGGAG

721    CTG
```
DNA sequence of IgG constant region (containing Fc-knob fragment) by artificial gene synthesis
SEQ ID NO: 53
```
  1    GACAAAACTC ACACATGCCC ACCGTGCCCA GCACCTGAAC TCCTGGGGGG ACCGTCAGTC

61    TTCCTCTTCC CCCCAAAACC CAAGGACACC CTCATGATCT CCCGGACCCC TGAGGTCACA

121    TGCGTGGTGG TGGACGTGAG CCACGAAGAC CCTGAGGTCA AGTTCAACTG GTACGTGGAC

181    GGCGTGGAGG TGCATAATGC CAAGACAAAG CCGCGGGAGG AGCAGTACGC AGCACGTAC

241    CGTGTGGTCA GCGTCCTCAC CGTCCTGCAC CAGGACTGGC TGAATGGCAA GGAGTACAAG

301    TGCAAGGTCT CCAACAAAGC CCTCCCAGCC CCCATCGAGA AAACCATCTC CAAAGCCAAA

361    GGGCAGCCCC GAGAACCACA GGTGTACACC CTGCCCCCAT CCCGGGATGA GCTGACCAAG
```

```
421        AACCAGGTCA GCCTGTGGTG CCTGGTCAAA GGCTTCTATC CCAGCGACAT CGCCGTGGAG

481        TGGGAGAGCA ATGGGCAGCC GGAGAACAAC TACAAGACCA CGCCTCCCGT GCTGGACTCC

541        GACGGCTCCT TCTTCCTCTA CAGCAAGCTC ACCGTGGACA AGAGCAGGTG GCAGCAGGGG

601        AACGTCTTCT CATGCTCCGT GATGCATGAG GCTCTGCACA ACCACTACAC GCAGAAGAGC

661        CTCTCCCTGT CTCCGGGTAAA
```

DNA sequence of anti-CD19-scFv by artificial gene synthesis

SEQ ID NO: 54

```
GATATCCAACTGACCCAGAGCCCCGCTAGCCTGGCCGTCAGCCTGGGCCAGAGGG
CCACCATTTCCTGCAAGGCTAGCCAGAGCGTCGACTACGACGGCGACTCCTACCT
GAACTGGTACCAGCAGATTCCTGGCCAGCCTCCCAAGCTGCTGATCTATGACGCCT
CCAATCTGGTGAGCGGCATCCCCCCCAGATTTTCCGGCAGCGGCTCCGGCACCGAT
TTTACCCTGAACATCCACCCCGTCGAGAAAGTGGATGCCGCCACCTACCACTGCCA
GCAGAGCACAGAGGATCCCTGGACCTTCGGAGGCGGCACAAAACTGGAAATCAA
GGGCGGCGGCGGAAGCGGAGGAGGAGGATCCGGAGGAGGCGGAAGCCAGGTGC
AGCTCCAGCAAAGCGGCGCCGAGCTGGTGAGACCCGGAAGCTCCGTGAAAATCA
GCTGCAAGGCCTCCGGCTACGCCTTCTCCTCCTACTGGATGAACTGGGTGAAGCA
GAGACCTGGACAAGGCCTCGAGTGGATCGGACAGATCTGGCCCGGCGACGGAGA
CACCAACTACAATGGCAAATTTAAAGGAAAAGCCACACTGACCGCTGACGAGAGC
TCCTCCACAGCCTATATGCAACTGAGCTCCCTGGCCTCCGAGGATAGCGCCGTCTA
CTTCTGCGCTAGGAGAGAGACCACCACCGTGGGCAGATATTACTACGCCATGGATT
ACTGGGGCCAGGGAACCACAGTGACAGTGAGCAGC
```

DNA sequence of anti-CD3-scFv by artificial gene synthesis

SEQ ID NO: 55

```
  1        GACATCAAAC TCCAACAGAG CGGAGCCGAA CTGGCCAGAC CCGGCGCCAG CGTGAAGATG

61        AGCTGCAAGA CCAGCGGCTA TACCTTCACC AGGTATACCA TGCATTGGGT GAAACAGAGA

121        CCCGGACAGG GACTGGAGTG GATCGGCTAC ATCAACCCCT CCAGGGGCTA CACCAATTAC

181        AACCAGAAAT TCAAGGACAA GGCCACCCTG ACCACCGACA AAAGCTCCTC CACAGCTTAC

241        ATGCAGCTGA GCTCCCTGAC AAGCGAAGAC AGCGCTGTGT ACTACTGCGC CAGGTACTAC

301        GATGACCATT ACTGCCTGGA CTATTGGGGA CAGGGCACCA CCCTCACAGT GAGCAGCGTC

361        GAGGGAGGCA GCGGAGGAAG CGGAGGATCC GGAGGCTCCG GAGGCGTGGA CGATATTCAG

421        CTGACCCAAT CCCCCGCCAT CATGTCCGCT AGCCCTGGCG AGAAGGTGAC CATGACATGC

481        AGAGCCAGCA GCAGCGTCTC CTACATGAAC TGGTATCAGC AGAAGTCCGG CACAAGCCCC

541        AAGAGGTGGA TTTACGACAC CAGCAAGGTG GCCTCCGGCG TGCCCTACAG GTTTAGCGGC

601        TCCGGCAGCG GAACAAGCTA CTCCCTGACC ATCTCCTCCA TGGAGGCTGA GGACGCCGCC

661        ACCTATTACT GTCAGCAGTG GAGCTCCAAC CCCCTGACCT TCGGAGCCGG CACCAAGCTG

721        GAGCTGAAG
```

---

What is claimed is:

1. An asymmetric bispecific antibody, comprising:
a first chain comprising, in order from the N-terminus to the C-terminus, a light chain variable region (VL) and a light chain constant region (CL);
a second chain comprising, in order from the N-terminus to the C-terminus, a heavy chain variable region (VH), a heavy chain constant region, and a single-chain variable fragment (scFv), wherein
the heavy chain constant region of the second chain comprises a CH1 domain and a Fc region,
the scFv of the second chain comprises, in order from the N-terminus to the C-terminus, a heavy chain variable region and a light chain variable region against a second antigen or epitope, or in order from the N-terminus to the C-terminus, a light chain variable region and a heavy chain variable region against a second antigen or epitope,
the VL and the CL of the first chain and the VH and the CH1 domain of the second chain together constitute an antigen-binding fragment (Fab) against a first antigen or epitope; and
a third chain comprising a heavy chain Fc region, wherein the heavy chain Fc region comprises an antibody hinge region, CH2 and CH3;
the light chain variable region of the first chain and the heavy chain variable region of the second chain specifically bind to the first antigen or epitope, and the scFv of the second chain specifically binds to the second antigen or epitope; and
the first antigen or epitope is CD89, and the VL of the first chain comprises the following CDRs: CDR1 having a sequence of SEQ ID NO: 9, CDR2 having a sequence of SEQ ID NO: 10, and CDR3 having a sequence of SEQ ID NO: 11, and the VH of the second chain comprises the following CDRs: CDR1 having a sequence of SEQ ID NO: 12, CDR2 having a sequence of SEQ ID NO: 13, and CDR3 having a sequence of SEQ ID NO: 14.

2. The antibody according to claim 1, wherein the second chain comprises a hinge region provided between the CH1 domain and the Fc region; the third chain comprises, in order from the N-terminus to the C-terminus, the hinge region and the heavy chain Fc region of the third strand; and an intermolecular disulfide bond is formed between the hinge region of the second chain and the hinge region of the third chain.

3. The antibody according to claim 2, wherein a disulfide bond is provided between the light chain constant region of the first chain and the heavy chain constant region of the second chain; and/or 0, 1 or 2 disulfide bond(s) is (are) provided between the CH3 domain of the second chain and the CH3 domain of the third chain.

4. The antibody according to claim 1, wherein an interface between the CH3 domain of the second chain and the CH3 domain of the third chain is subjected to a modification to reduce the formation of a homodimer, wherein the modification is:

a) substituting an amino acid residue at the interface of the CH3 domain of the second chain with an amino acid residue having a large side chain to generate a knob on the interface side of the second chain,
b) substituting an amino acid residue at the interface of the CH3 domain of the third chain with an amino acid residue having a small side chain to generate a hole on the interface side of the third chain,
wherein the knob is positioned in the hole; or
a) substituting an amino acid residue at the interface of the CH3 domain of the second chain with an amino acid residue having a small side chain to generate a hole on the interface side of the second chain,
b) substituting an amino acid residue at the interface of the CH3 domain of the third chain with an amino acid residue having a large side chain to generate a knob on the interface side of the third chain,
wherein the knob is positioned in the hole.

5. The antibody according to claim 4, wherein the amino acid residue having a large side chain is selected from the group consisting of arginine (R), phenylalanine (F), tyrosine (Y), and tryptophan (W); and
the amino acid residue having a small side chain is selected from the group consisting of alanine (A), serine (S), threonine (T), and proline (V).

6. The antibody according to claim 1, wherein the Fc region of the second chain and/or the Fc region of the third chain are further modified to eliminate the antibody-dependent cell-mediated cytotoxicity (ADCC), by mutating Asn at position 297 to Ala.

7. The antibody according to claim 1, wherein the first antigen or epitope is different from the second antigen or epitope.

8. The antibody according to claim 1, wherein the second antigen or epitope is a surface antigen or epitope of an immune effector cell, selected from the group consisting of FcγRI (CD64), FcγRIIA (CD32), FcγRIIB (CD32), FcγRIIIA (CD16a), FcγRIIIB (CD16b), FcαRI (CD89), CD3, and PD1.

9. The antibody according to claim 1, which is an anti-CD89/CD20 bispecific antibody, wherein the first chain has a sequence of SEQ ID NO: 1, the VH and CH1 of the second chain have a sequence of SEQ ID NO: 2, the scFv of the second chain has a sequence of SEQ ID NO: 3, and one of the Fc region of the second chain and the Fc region of the third chain has a sequence of SEQ ID NO: 4 or 49 and the other has a sequence of SEQ ID NO: 5 or 50.

10. The antibody according to claim 1, wherein the Fc region of the second chain is linked to the scFv region of the second chain via a peptide linker comprising 0, 1, 2, or 3 GGGGS.

11. The antibody according to claim 7, wherein the second antigen or epitope is CD20, and the scFv of the second chain has a sequence of SEQ ID NO: 3; or
wherein the second antigen or epitope is CD3 and the scFv of the second chain has a sequence of SEQ ID NO: 8.

12. The antibody according to claim 1, wherein the antibody comprises a heavy chain variable region having an amino acid sequence of SEQ ID NO: 23 and a light chain variable region having an amino acid sequence of SEQ ID NO: 24.

13. A pharmaceutical composition, comprising the antibody according to claim 1 and at least one pharmaceutically acceptable excipient.

14. A method of treating a cancer or a tumor, comprising administrating an effective amount of the antibody according to claim 1 to the subject in need thereof.

15. The method according to claim 14, wherein the first antigen or epitope is expressed on the cell surface of the cancer or the tumor.

16. The method according to claim 14, wherein the cancer or the tumor is selected from B lymphocyte tumor, non-Hodgkin's lymphoma, leukemia, lung cancer, gastric cancer, liver cancer, breast cancer, esophageal cancer, intestinal cancer, melanoma, kidney cancer, pancreatic cancer, prostate cancer, bladder cancer, head and neck cancer, and cervical cancer.

17. The antibody according to claim 3, wherein the disulfide bond(s) is (are) provided by introducing cysteine at corresponding positions between the second heavy chain variable region of the second chain and the light chain variable region of the second chain, and/or between the CH3 domain of the second chain and the CH3 domain of the third chain.

* * * * *

SEQUENCE LISTING

<160> NUMBER OF SEQ ID NOS: 55

<210> SEQ ID NO 1
<211> LENGTH: 214
<212> TYPE: PRT
<213> ORGANISM: Artificial Sequence
<220> FEATURE:

<223> OTHER INFORMATION: Amino acid sequence of the first chain
(antibody VL and CL of anti-CD89 light chain)

<400> SEQUENCE: 1

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Glu Arg Phe Ser Gly
50                  55                  60

Ser Arg Ser Gly Ser His Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 219
<212> TYPE: PRT
<213> ORGANISM: Artificial Sequence
<220> FEATURE:
<223> OTHER INFORMATION: Amino acid sequence of antibody VH and CH1 of
anti-CD89 heavy chain in the second chain

<400> SEQUENCE: 2

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Val Phe Thr Asn Tyr
            20                  25                  30

Gly Met Asn Trp Val Lys Gln Thr Pro Gly Lys Gly Leu Lys Trp Met
        35                  40                  45

Gly Trp Ile Asn Thr Tyr Thr Gly Arg Pro Thr Ser Ala Asp Asp Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Ser Gln Gly Phe Ser Phe Thr Ser Trp Gly Gln Gly Thr Leu Val
            100                 105                 110

Thr Val Ser Ala Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys
210                 215

<210> SEQ ID NO 3
<211> LENGTH: 241
<212> TYPE: PRT
<213> ORGANISM: Artificial Sequence
<220> FEATURE:
<223> OTHER INFORMATION: Amino acid sequence of scFv region of the
      second chain (ScFv of anti-CD20)

<400> SEQUENCE: 3

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
            85                  90                  95

Ala Arg Val Val Tyr Tyr Ser Asn Ser Tyr Trp Tyr Phe Asp Val Trp
            100                 105                 110

Gly Thr Gly Thr Thr Val Thr Val Ser Gly Gly Gly Gly Ser Gly Gly
            115                 120                 125

Gly Gly Ser Gly Gly Gly Gly Ser Gln Ile Val Leu Ser Gln Ser Pro
            130                 135                 140

Ala Ile Leu Ser Ala Ser Pro Gly Glu Lys Val Thr Met Thr Cys Arg
145                 150                 155                 160

Ala Ser Ser Ser Val Ser Tyr Met His Trp Tyr Gln Gln Lys Pro Gly
            165                 170                 175

Ser Ser Pro Lys Pro Trp Ile Tyr Ala Pro Ser Asn Leu Ala Ser Gly
            180                 185                 190

Val Pro Ala Arg Phe Ser Gly Ser Gly Ser Gly Thr Ser Tyr Ser Leu
            195                 200                 205

Thr Ile Ser Arg Val Glu Ala Glu Asp Ala Ala Thr Tyr Tyr Cys Gln
            210                 215                 220

Gln Trp Ser Phe Asn Pro Pro Thr Phe Gly Ala Gly Thr Lys Leu Glu
225                 230                 235                 240

Leu

<210> SEQ ID NO 4
<211> LENGTH: 227
<212> TYPE: PRT
<213> ORGANISM: Artificial Sequence
<220> FEATURE:
<223> OTHER INFORMATION: Amino acid sequence of Fc region of the second
      chain (Fc-Hole fragment)

<400> SEQUENCE: 4

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Ala Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 5
<211> LENGTH: 227
<212> TYPE: PRT
<213> ORGANISM: Artificial Sequence
<220> FEATURE:
<223> OTHER INFORMATION: Amino acid sequence of Fc region of the third
      chain (Fc-Knob fragment)

<400> SEQUENCE: 5

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

```
His Asn Ala Lys Thr Lys Pro Arg Glu Glu Gln Tyr Ala Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 6
<211> LENGTH: 218
<212> TYPE: PRT
<213> ORGANISM: Artificial Sequence
<220> FEATURE:
<223> OTHER INFORMATION: Amino acid sequence of the sequence of the
      first chain (antibody VL and CL of anti-CD19 light chain)

<400> SEQUENCE: 6

Asp Ile Gln Leu Thr Gln Ser Pro Ala Ser Leu Ala Val Ser Leu Gly
  1               5                  10                  15

Gln Arg Ala Thr Ile Ser Cys Lys Ala Ser Gln Ser Val Asp Tyr Asp
                 20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
        50                  55                  60

Arg Phe Ser Gly Ser Gly Ser Gly Thr Asp Phe Thr Leu Asn Ile His
 65                  70                  75                  80

Pro Val Glu Lys Val Asp Ala Ala Thr Tyr His Cys Gln Gln Ser Thr
                 85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190
```

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 7
<211> LENGTH: 227
<212> TYPE: PRT
<213> ORGANISM: Artificial Sequence
<220> FEATURE:
<223> OTHER INFORMATION: Amino acid sequence of antibody VH and CH1 of
      anti-CD19 heavy chain in the second chain

<400> SEQUENCE: 7

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys
225

<210> SEQ ID NO 8
<211> LENGTH: 243
<212> TYPE: PRT
<213> ORGANISM: Artificial Sequence
<220> FEATURE:
<223> OTHER INFORMATION: Amino acid sequence of scFv region of the
      second chain (ScFv of anti-CD3)

<400> SEQUENCE: 8

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

```
Thr Met His Trp Val Lys Gln Arg Pro Gly Gln Gly Leu Glu Trp Ile
        35                  40                  45
Gly Tyr Ile Asn Pro Ser Arg Gly Tyr Thr Asn Tyr Asn Gln Lys Phe
    50                  55                  60
Lys Asp Lys Ala Thr Leu Thr Thr Asp Lys Ser Ser Ser Thr Ala Tyr
65                  70                  75                  80
Met Gln Leu Ser Ser Leu Thr Ser Glu Asp Ser Ala Val Tyr Tyr Cys
                85                  90                  95
Ala Arg Tyr Tyr Asp Asp His Tyr Cys Leu Asp Tyr Trp Gly Gln Gly
            100                 105                 110
Thr Thr Leu Thr Val Ser Val Glu Gly Gly Ser Gly Gly Ser Gly Gly
        115                 120                 125
Gly Ser Gly Gly Ser Gly Gly Val Asp Asp Ile Gln Leu Thr Gln Ser
    130                 135                 140
Pro Ala Ile Met Ser Ala Ser Pro Gly Glu Lys Val Thr Met Thr Cys
145                 150                 155                 160
Arg Ala Ser Ser Ser Val Ser Tyr Met Asn Trp Tyr Gln Gln Lys Ser
                165                 170                 175
Gly Thr Ser Pro Lys Arg Trp Ile Tyr Asp Thr Ser Lys Val Ala Ser
            180                 185                 190
Gly Val Pro Tyr Arg Phe Ser Gly Ser Gly Ser Gly Thr Ser Tyr Ser
        195                 200                 205
Leu Thr Ile Ser Ser Met Glu Ala Glu Asp Ala Ala Thr Tyr Tyr Cys
    210                 215                 220
Gln Gln Trp Ser Ser Asn Pro Leu Thr Phe Gly Ala Gly Thr Lys Leu
225                 230                 235                 240
Glu Leu Lys

<210> SEQ ID NO 9
<211> LENGTH: 6
<212> TYPE: PRT
<213> ORGANISM: Mus musculus
<220> FEATURE:
<223> OTHER INFORMATION: VL of anti-CD89 antibody CDR1

<400> SEQUENCE: 9

Gln Asp Ile Gly Ser Ser
1               5

<210> SEQ ID NO 10
<211> LENGTH: 3
<212> TYPE: PRT
<213> ORGANISM: Mus musculus
<220> FEATURE:
<223> OTHER INFORMATION: VL of anti-CD89 antibody CDR2

<400> SEQUENCE: 10

Ala Thr Ser
1

<210> SEQ ID NO 11
<211> LENGTH: 9
<212> TYPE: PRT
<213> ORGANISM: Mus musculus
<220> FEATURE:
<223> OTHER INFORMATION: VL of anti-CD89 antibody CDR3

<400> SEQUENCE: 11

Leu Gln Tyr Ala Ser Tyr Pro Trp Thr
```

<210> SEQ ID NO 12
<211> LENGTH: 8
<212> TYPE: PRT
<213> ORGANISM: Mus musculus
<220> FEATURE:
<223> OTHER INFORMATION: VH of anti-CD89 antibody CDR1

<400> SEQUENCE: 12

Gly Tyr Val Phe Thr Asn Tyr Gly
1               5

<210> SEQ ID NO 13
<211> LENGTH: 8
<212> TYPE: PRT
<213> ORGANISM: Mus musculus
<220> FEATURE:
<223> OTHER INFORMATION: VH of anti-CD89 antibody CDR2

<400> SEQUENCE: 13

Ile Asn Thr Tyr Thr Gly Arg Pro
1               5

<210> SEQ ID NO 14
<211> LENGTH: 9
<212> TYPE: PRT
<213> ORGANISM: Mus musculus
<220> FEATURE:
<223> OTHER INFORMATION: VH of anti-CD89 antibody CDR3

<400> SEQUENCE: 14

Ser Ser Gln Gly Phe Ser Phe Thr Ser
1               5

<210> SEQ ID NO 15
<211> LENGTH: 10
<212> TYPE: PRT
<213> ORGANISM: Mus musculus
<220> FEATURE:
<223> OTHER INFORMATION: VL of anti-CD19 antibody CDR1

<400> SEQUENCE: 15

Gln Ser Val Asp Tyr Asp Gly Asp Ser Tyr
1               5                   10

<210> SEQ ID NO 16
<211> LENGTH: 3
<212> TYPE: PRT
<213> ORGANISM: Mus musculus
<220> FEATURE:
<223> OTHER INFORMATION: VL of anti-CD19 antibody CDR2

<400> SEQUENCE: 16

Asp Ala Ser
1

<210> SEQ ID NO 17
<211> LENGTH: 9
<212> TYPE: PRT
<213> ORGANISM: Mus musculus
<220> FEATURE:
<223> OTHER INFORMATION: VL of anti-CD19 antibody CDR3

<400> SEQUENCE: 17

Gln Gln Ser Thr Glu Asp Pro Trp Thr
1               5

<210> SEQ ID NO 18
<211> LENGTH: 8
<212> TYPE: PRT
<213> ORGANISM: Mus musculus
<220> FEATURE:
<223> OTHER INFORMATION: VH of anti-CD19 antibody CDR1

<400> SEQUENCE: 18

Gly Tyr Ala Phe Ser Ser Tyr Trp
1               5

<210> SEQ ID NO 19
<211> LENGTH: 8
<212> TYPE: PRT
<213> ORGANISM: Mus musculus
<220> FEATURE:
<223> OTHER INFORMATION: VH of anti-CD19 antibody CDR2

<400> SEQUENCE: 19

Ile Trp Pro Gly Asp Gly Asp Thr
1               5

<210> SEQ ID NO 20
<211> LENGTH: 17
<212> TYPE: PRT
<213> ORGANISM: Mus musculus
<220> FEATURE:
<223> OTHER INFORMATION: VH of anti-CD19 antibody CDR3

<400> SEQUENCE: 20

Ala Arg Arg Glu Thr Thr Thr Val Gly Arg Tyr Tyr Tyr Ala Met Asp
1               5                   10                  15

Tyr

<210> SEQ ID NO 21
<211> LENGTH: 426
<212> TYPE: DNA
<213> ORGANISM: Mus musculus
<220> FEATURE:
<223> OTHER INFORMATION: DNA sequence of variable region of anti-CD89
      heavy chain

<400> SEQUENCE: 21
atggtcagct actgggacac cggggtcctg ctgtgcgcgc tgctcagctg tctgcttctc      60
acaggatcta gttccggaca gatccagttg gtgcaatctg gacctgagct gaagaagccc     120
ggagagacag tcaagatctc ctgcaaggct tcggggtatg tcttcacaaa ctatggaatg     180
aactgggtga agcagactcc aggaaagggt ttaaagtgga tgggctggat aaacacctac     240 actgcaggc caacatctgc tgatgacttc aagggacggt tgccttctc tttggaaacc     300 tctgccagca ctgcctattt gcagatcaac aacctcaaaa atgaggacac ggctacatat     360
ttctgttcaa gccagggggtt ttcgtttact tcctggggcc aggggactct ggtcactgtc     420
tctgca                                                                426

<210> SEQ ID NO 22
<211> LENGTH: 399
<212> TYPE: DNA
<213> ORGANISM: Mus musculus
<220> FEATURE:
<223> OTHER INFORMATION: DNA sequence of variable region of anti-CD89
      light chain

<400> SEQUENCE: 22

```
atggtcagct actgggacac cggggtcctg ctgtgcgcgc tgctcagctg tctgcttctc      60
acaggatcta gttccggaga catccagatg acccagtctc catcctcctt atctgcctct     120
ctgggagaaa gagtcagtct cacttgtcgg gcaagtcagg acattggtag tagtttaaac     180
tggcttcagc aggaaccaga tggaactatt aaacgcctga tctacgccac atccagttta     240
gattctggtg tccccgaaag gttcagtggc agtaggtctg ggtcacatta ttctctcacc     300
atcagcagcc ttgagtctga agattttgta gactattact gtctacaata tgctagttat     360
ccgtggacgt tcggtggagg caccaagctg gaaatcaaa                            399
```

<210> SEQ ID NO 23
<211> LENGTH: 116
<212> TYPE: PRT
<213> ORGANISM: Mus musculus
<220> FEATURE:
<223> OTHER INFORMATION: Amino acid sequence of variable region of
      anti-CD89 heavy chain

<400> SEQUENCE: 23

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Val Phe Thr Asn Tyr
            20                  25                  30

Gly Met Asn Trp Val Lys Gln Thr Pro Gly Lys Gly Leu Lys Trp Met
        35                  40                  45

Gly Trp Ile Asn Thr Tyr Thr Gly Arg Pro Thr Ser Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Ser Gln Gly Phe Ser Phe Thr Ser Trp Gly Gln Gly Thr Leu Val
            100                 105                 110

Thr Val Ser Ala
        115
```

<210> SEQ ID NO 24
<211> LENGTH: 107
<212> TYPE: PRT
<213> ORGANISM: Mus musculus
<220> FEATURE:
<223> OTHER INFORMATION: Amino acid sequence of variable region of
      anti-CD89 light chain

<400> SEQUENCE: 24

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
            20                  25                  30

Leu Asn Trp Leu Gln Gln Glu Pro Asp Gly Thr Ile Lys Arg Leu Ile
        35                  40                  45

Tyr Ala Thr Ser Ser Leu Asp Ser Gly Val Pro Glu Arg Phe Ser Gly
    50                  55                  60

Ser Arg Ser Gly Ser His Tyr Ser Leu Thr Ile Ser Ser Leu Glu Ser
65                  70                  75                  80

Glu Asp Phe Val Asp Tyr Tyr Cys Leu Gln Tyr Ala Ser Tyr Pro Trp
                85                  90                  95
```

Thr Phe Gly Gly Gly Thr Lys Leu Glu Ile Lys
            100                 105

<210> SEQ ID NO 25
<211> LENGTH: 55
<212> TYPE: DNA
<213> ORGANISM: Artificial Sequence
<220> FEATURE:
<223> OTHER INFORMATION: CD89 VL upstream primer

<400> SEQUENCE: 25
taagcttggt accgagctcg gatccgccgc caccatggtc agctactggg acacc        55

<210> SEQ ID NO 26
<211> LENGTH: 40
<212> TYPE: DNA
<213> ORGANISM: Artificial Sequence
<220> FEATURE:
<223> OTHER INFORMATION: CD89 VL downstream primer

<400> SEQUENCE: 26
gatggtgcag ccacagttcg tttgatttcc agcttggtgc        40

<210> SEQ ID NO 27
<211> LENGTH: 40
<212> TYPE: DNA
<213> ORGANISM: Artificial Sequence
<220> FEATURE:
<223> OTHER INFORMATION: CL upstream primer

<400> SEQUENCE: 27
gcaccaagct ggaaatcaaa cgaactgtgg ctgcaccatc        40

<210> SEQ ID NO 28
<211> LENGTH: 59
<212> TYPE: DNA
<213> ORGANISM: Artificial Sequence
<220> FEATURE:
<223> OTHER INFORMATION: CL down stream primer

<400> SEQUENCE: 28
gcgggccctc tagactcgag cggccgcgtc gacctaacac tctcccctgt tgaagctct    59

<210> SEQ ID NO 29
<211> LENGTH: 55
<212> TYPE: DNA
<213> ORGANISM: Artificial Sequence
<220> FEATURE:
<223> OTHER INFORMATION: CD89 VH upstream primer

<400> SEQUENCE: 29
taagcttggt accgagctcg gatccgccgc caccatggtc agctactggg acacc        55

<210> SEQ ID NO 30
<211> LENGTH: 40
<212> TYPE: DNA
<213> ORGANISM: Artificial Sequence
<220> FEATURE:
<223> OTHER INFORMATION: CD89 VH downstream primer

<400> SEQUENCE: 30
gatgggccct tggtggaggc tgcagagaca gtgaccagag        40

<210> SEQ ID NO 31
<211> LENGTH: 40
<212> TYPE: DNA

<213> ORGANISM: Artificial Sequence
<220> FEATURE:
<223> OTHER INFORMATION: human IgG constant upstream primer

<400> SEQUENCE: 31
ctctggtcac tgtctctgca gcctccacca agggcccatc             40

<210> SEQ ID NO 32
<211> LENGTH: 34
<212> TYPE: DNA
<213> ORGANISM: Artificial Sequence
<220> FEATURE:
<223> OTHER INFORMATION: human IgG constant downstream primerr

<400> SEQUENCE: 32
tttacccgga gacagggaga ggctcttctg cgtg                   34

<210> SEQ ID NO 33
<211> LENGTH: 53
<212> TYPE: DNA
<213> ORGANISM: Artificial Sequence
<220> FEATURE:
<223> OTHER INFORMATION: CD20 scFv upstream primer

<400> SEQUENCE: 33
gtggtggtag cggtggcggt ggtagtcagg cttatttgca acagtctggc gcg    53

<210> SEQ ID NO 34
<211> LENGTH: 54
<212> TYPE: DNA
<213> ORGANISM: Artificial Sequence
<220> FEATURE:
<223> OTHER INFORMATION: CD20 scFv downstream primer

<400> SEQUENCE: 34
ccaagctgga gctggaatag gtcgacgcgg ccgctcgagt ctagagggcc cgcg    54

<210> SEQ ID NO 35
<211> LENGTH: 53
<212> TYPE: DNA
<213> ORGANISM: Artificial Sequence
<220> FEATURE:
<223> OTHER INFORMATION: human Fc knob upstream primer

<400> SEQUENCE: 35
aagcttggta ccgagctcgg atccgccgcc accatggtca gctactggga cac    53

<210> SEQ ID NO 36
<211> LENGTH: 58
<212> TYPE: DNA
<213> ORGANISM: Artificial Sequence
<220> FEATURE:
<223> OTHER INFORMATION: human Fc-knob downstream primer

<400> SEQUENCE: 36
cgcgggccct ctagactcga gcggccgcgt cgacctattt acccggagac agggagag    58

<210> SEQ ID NO 37
<211> LENGTH: 111
<212> TYPE: PRT
<213> ORGANISM: Mus musculus
<220> FEATURE:
<223> OTHER INFORMATION: Amino acid sequence of variable region of
      anti-CD19 light chain

<400> SEQUENCE: 37

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Leu Asn Trp Tyr Gln Gln Ile Pro Gly Gln Pro Pro
            35                  40                  45

Lys Leu Leu Ile Tyr Asp Ala Ser Asn Leu Val Ser Gly Ile Pro Pro
50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110

<210> SEQ ID NO 38
<211> LENGTH: 124
<212> TYPE: PRT
<213> ORGANISM: Mus musculus
<220> FEATURE:
<223> OTHER INFORMATION: Amino acid sequence of variable region of
      anti-CD19 heavy chain

<400> SEQUENCE: 38

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
            35                  40                  45

Gly Gln Ile Trp Pro Gly Asp Gly Asp Thr Asn Tyr Asn Gly Lys Phe
50                  55                  60

Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
            115                 120

<210> SEQ ID NO 39
<211> LENGTH: 50
<212> TYPE: DNA
<213> ORGANISM: Artificial Sequence
<220> FEATURE:
<223> OTHER INFORMATION: CD19 VL upstream primer

<400> SEQUENCE: 39
gtctgcttct cacaggatct agttccggag atatccaact gacccagagc        50

<210> SEQ ID NO 40
<211> LENGTH: 40
<212> TYPE: DNA
<213> ORGANISM: Artificial Sequence
<220> FEATURE:
<223> OTHER INFORMATION: CD19 VL downstream primer

<400> SEQUENCE: 40
gatggtgcag ccacagttcg cttgatttcc agttttgtgc                   40

<210> SEQ ID NO 41
<211> LENGTH: 42
<212> TYPE: DNA
<213> ORGANISM: Artificial Sequence
<220> FEATURE:
<223> OTHER INFORMATION: CL upstream primer

<400> SEQUENCE: 41
aaactggaaa tcaagcgaac tgtggctgca ccatctgtct tc    42

<210> SEQ ID NO 42
<211> LENGTH: 59
<212> TYPE: DNA
<213> ORGANISM: Artificial Sequence
<220> FEATURE:
<223> OTHER INFORMATION: CL downstream primer

<400> SEQUENCE: 42
gcgggccctc tagactcgag cggccgcgtc gacctaacac tctcccctgt tgaagctct    59

<210> SEQ ID NO 43
<211> LENGTH: 49
<212> TYPE: DNA
<213> ORGANISM: Artificial Sequence
<220> FEATURE:
<223> OTHER INFORMATION: CD19 VH upstream primer

<400> SEQUENCE: 43
tctgcttctc acaggatcta gttccggaca ggtgcagctc cagcaaagc    49

<210> SEQ ID NO 44
<211> LENGTH: 40
<212> TYPE: DNA
<213> ORGANISM: Artificial Sequence
<220> FEATURE:
<223> OTHER INFORMATION: CD19 VH downstream primer

<400> SEQUENCE: 44
gatgggccct tggtggaggc gctgctcact gtcactgtgg    40

<210> SEQ ID NO 45
<211> LENGTH: 48
<212> TYPE: DNA
<213> ORGANISM: Artificial Sequence
<220> FEATURE:
<223> OTHER INFORMATION: human IgG constant upstream primer

<400> SEQUENCE: 45
gggaaccaca gtgacagtga gcagcgcctc caccaagggc ccatcggt    48

<210> SEQ ID NO 46
<211> LENGTH: 34
<212> TYPE: DNA
<213> ORGANISM: Artificial Sequence
<220> FEATURE:
<223> OTHER INFORMATION: human IgG constant downstream primer

<400> SEQUENCE: 46
tttacccgga gacagggaga ggctcttctg cgtg    34

<210> SEQ ID NO 47
<211> LENGTH: 37
<212> TYPE: DNA
<213> ORGANISM: Artificial Sequence
<220> FEATURE:

<223> OTHER INFORMATION: CD3 scFv upstream primer

<400> SEQUENCE: 47
ggtagtgaca tcaaactcca acagagcgga gccgaac            37

<210> SEQ ID NO 48
<211> LENGTH: 58
<212> TYPE: DNA
<213> ORGANISM: Artificial Sequence
<220> FEATURE:
<223> OTHER INFORMATION: CD3 scFv downstream primer

<400> SEQUENCE: 48
gcgggccctc tagactcgag cggccgcgtc gacctacttc agctccagct tggtgccg            58

<210> SEQ ID NO 49
<211> LENGTH: 227
<212> TYPE: PRT
<213> ORGANISM: Artificial
<220> FEATURE:
<223> OTHER INFORMATION: Sequence of Fc region of the second chain
      containing no mutation from Asn at position 297 to Ala in Fc
      region (Fc-hole fragment)

<400> SEQUENCE: 49

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 50
<211> LENGTH: 227
<212> TYPE: PRT

<213> ORGANISM: Artificial
<220> FEATURE:
<223> OTHER INFORMATION: Sequence of Fc region of the third chain
      containing no mutation from Asn at position 297 to Ala in Fc
      region (Fc-knob fragment)

<400> SEQUENCE: 50

Asp Lys Thr His Thr Cys Pro Pro Cys Pro Ala Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 51
<211> LENGTH: 990
<212> TYPE: DNA
<213> ORGANISM: Artificial
<220> FEATURE:
<223> OTHER INFORMATION: DNA sequence of IgG constant region (containing
      Fc-hole fragment) by artificial gene synthesis

<400> SEQUENCE: 51
gcctccacca agggcccatc ggtcttcccc ctggcaccct cctccaagag cacctctggg      60
ggcacagcag ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agttgagccc     300
aaatcttgtg acaaaactca cacatgccca ccgtgcccag cacctgaact cctggggga      360 ccgtcagtct tcctcttccc cccaaaaccc aaggacaccc tcatgatctc ccggaccct      420 gaggtcacat gcgtggtggt ggacgtgagc cacgaagacc ctgaggtcaa gttcaactgg     480

```
tacgtggacg gcgtggaggt gcataatgcc aagacaaagc cgcgggagga gcagtacaac      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggatgag      720
ctgaccaaga accaggtcag cctgtcctgc gcggtcaaag gcttctatcc cagcgacatc      780
gccgtggagt gggagagcaa tgggcagccg gagaacaact acaagaccac gcctcccgtg      840
ctggactccg acggctcctt cttcctcgtc agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa      990
```

```
<210> SEQ ID NO 52
<211> LENGTH: 723
<212> TYPE: DNA
<213> ORGANISM: Artificial
<220> FEATURE:
<223> OTHER INFORMATION: DNA sequence of anti-CD20-scFv by artificial
      gene synthesis

<400> SEQUENCE: 52
caggcttatt tgcaacagtc tggcgcggaa cttgtaagac caggggcttc tgtgaagatg       60
agctgcaagg ctagtggata cattcacg tcctataata tgcactgggt caagcagact      120
ccccggcaag gcctggaatg gatcggagca atctaccctg gtaacggaga tacctcctat      180
aatcagaaat tcaaggggaa agccacccct accgtggata atctagtag caccgcctac      240 atgcagctgt cctcactcac atcagaggac tccgccgtct acttctgtgc ccgcgtggtt      300
tactattcaa acagctactg gtactttgac gttgggga caggcaccac tgtgactgtg      360
agcggtggtg gtggttctgg cggcggcggc tccggtggtg gtggttctca aattgtgctg      420
tcccagtccc cggccatcct ttcagccagt ccaggagaaa aagtcacgat gacctgtaga      480
gcttcctcaa gtgtgtctta tatgcactgg tatcagcaga gccaggatc atctcccaaa      540 ccatggatat acgcccttc caatctcgcc agcggagtcc ctgcacgctt cagcggtagc      600
ggctctggga cttcttacag tctcactatc agtagggtgg aagctgagga cgcagccaca      660
tactattgcc agcaatggag cttaacccc cccacattcg gcgctggcac caagctggag      720
ctg                                                                    723
```

```
<210> SEQ ID NO 53
<211> LENGTH: 681
<212> TYPE: DNA
<213> ORGANISM: Artificial
<220> FEATURE:
<223> OTHER INFORMATION: DNA sequence of IgG constant region (containing
      Fc-knob fragment) by artificial gene synthesis

<400> SEQUENCE: 53
gacaaaactc acacatgccc accgtgccca gcacctgaac tcctgggggg accgtcagtc       60
ttcctcttcc ccccaaaacc caaggacacc ctcatgatct cccggacccc tgaggtcaca      120
tgcgtggtgg tggacgtgag ccacgaagac cctgaggtca agttcaactg gtacgtggac      180
ggcgtggagg tgcataatgc caagacaaag ccgcgggagg agcagtacgc cagcacgtac      240
cgtgtggtca gcgtcctcac cgtcctgcac caggactggc tgaatggcaa ggagtacaag      300
tgcaaggtct ccaacaaagc cctcccagcc cccatcgaga aaaccatctc caaagccaaa      360
```

| | |
|---|---|
| gggcagcccc gagaaccaca ggtgtacacc ctgcccccat cccgggatga gctgaccaag | 420 |
| aaccaggtca gcctgtggtg cctggtcaaa ggcttctatc ccagcgacat cgccgtggag | 480 |
| tgggagagca atgggcagcc ggagaacaac tacaagacca cgcctcccgt gctggactcc | 540 |
| gacggctcct tcttcctcta cagcaagctc accgtggaca gagcaggtg gcagcagggg | 600 |
| aacgtcttct catgctccgt gatgcatgag gctctgcaca accactacac gcagaagagc | 660 |
| ctctcccctgt ctccgggtaa a | 681 |

<210> SEQ ID NO 54
<211> LENGTH: 750
<212> TYPE: DNA
<213> ORGANISM: Artificial
<220> FEATURE:
<223> OTHER INFORMATION: DNA sequence of anti-CD19-scFv by artificial gene synthesis

<400> SEQUENCE: 54

| | |
|---|---|
| gatatccaac tgacccagag ccccgctagc ctggccgtca gcctgggcca gagggccacc | 60 |
| atttcctgca aggctagcca gagcgtcgac tacgacggcg actcctacct gaactggtac | 120 |
| cagcagattc ctggccagcc tcccaagctg ctgatctatg acgcctccaa tctggtgagc | 180 |
| ggcatccccc ccagattttc cggcagcggc tccggcaccg atttaccct gaacatccac | 240 |
| cccgtcgaga agtggatgc cgccacctac cactgccagc agagcacaga ggatccctgg | 300 |
| accttcggag cggcacaaa actggaaatc aagggcggcg gcggaagcgg aggaggagga | 360 |
| tccggaggag gcggaagcca ggtgcagctc cagcaaagcg cgccgagct ggtgagaccc | 420 |
| ggaagctccg tgaaaatcag ctgcaaggcc tccggctacg ccttctcctc ctactggatg | 480 |
| aactgggtga agcagagacc tggacaaggc ctcgagtgga tcggacagat ctggcccggc | 540 |
| gacggagaca ccaactacaa tggcaaattt aaaggaaaag ccacactgac cgctgacgag | 600 |
| agctcctcca cagcctatat gcaactgagc tccctggcct ccgaggatag cgccgtctac | 660 |
| ttctgcgcta ggagagagac caccaccgtg ggcagatatt actacgccat ggattactgg | 720 |
| ggccagggaa ccacagtgac agtgagcagc | 750 |

<210> SEQ ID NO 55
<211> LENGTH: 729
<212> TYPE: DNA
<213> ORGANISM: Artificial
<220> FEATURE:
<223> OTHER INFORMATION: DNA sequence of anti-CD3-scFv by artificial gene synthesis

<400> SEQUENCE: 55

| | |
|---|---|
| gacatcaaac tccaacagag cggagccgaa ctggccagac ccggcgccag cgtgaagatg | 60 |
| agctgcaaga ccagcggcta ccttcacc aggtataccca tgcattgggt gaaacagaga | 120 |
| cccggacagg gactggagtg gatcggctac atcaaccccct ccaggggcta caccaattac | 180 |
| aaccagaaat tcaaggacaa ggccaccctg accaccgaca aaagctcctc cacagcttac | 240 |
| atgcagctga gctccctgac aagcgaagac agcgctgtgt actactgcgc caggtactac | 300 |
| gatgaccatt actgcctgga ctattgggga cagggcacca ccctcacagt gagcagcgtc | 360 |
| gagggaggca gcggaggaag cggaggatcc ggaggctccg gaggcgtgga cgatattcag | 420 |
| ctgacccaat ccccgccat catgtccgct agcctggcg agaaggtgac catgacatgc | 480 |
| agagccagca gcagcgtctc ctacatgaac tggtatcagc agaagtccgg cacaagcccc | 540 |
| aagaggtgga tttacgacac cagcaaggtg gcctccggcg tgccctacag gtttagcggc | 600 |

```
tccggcagcg gaacaagcta ctccctgacc atctcctcca tggaggctga ggacgccgcc      660
acctattact gtcagcagtg gagctccaac cccctgacct tcggagccgg caccaagctg      720
gagctgaag                                                              729
```